United States Patent [19]

Numata et al.

[11] 4,379,924
[45] Apr. 12, 1983

[54] CEPHALOSPORIN DERIVATIVES

[75] Inventors: Mitsuo Numata, Takatsuki; Isao Mimamida, Kyoto; Masayoshi Yamaoka, Osaka; Mitsura Shiraishi, Suita; Toshio Miyawaki, Nishinomiya, all of Japan

[73] Assignee: Takeda Chemical Industries, Ltd., Osaka, Japan

[21] Appl. No.: 863,719

[22] Filed: Dec. 23, 1977

Related U.S. Application Data

[62] Division of Ser. No. 534,782, Dec. 20, 1974, Pat. No. 4,080,498.

[30] Foreign Application Priority Data

Dec. 25, 1973 [JP] Japan ................................. 48-1521
Feb. 20, 1974 [JP] Japan ................................. 49-20752
Apr. 15, 1974 [JP] Japan ................................. 49-42574
Jul. 17, 1974 [JP] Japan ................................. 49-82623
Nov. 13, 1974 [JP] Japan ................................. 49-131381

[51] Int. Cl.³ ................. C07D 501/36; A61K 31/545
[52] U.S. Cl. ..................................... 544/27; 424/246
[58] Field of Search ............... 544/25, 27, 28, 26, 544/21, 15; 424/246

[56] References Cited

U.S. PATENT DOCUMENTS 3,516,997  6/1970  Takano et al. ..................... 544/27
3,926,984  12/1975  Teller et al. ...................... 544/22
4,077,965  3/1978  Kamiya et al. ................... 544/27
4,080,498  3/1978  Numata et al. ................... 544/27

FOREIGN PATENT DOCUMENTS 1461948  1/1977  United Kingdom .

*Primary Examiner*—Nicholas S. Rizzo
*Attorney, Agent, or Firm*—Antonelli, Terry & Wands

[57] ABSTRACT

A compound of the formula:

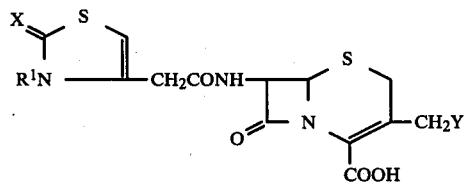

wherein $R^1$ represents hydrogen or an alkyl group, X represents oxygen or sulfur or a group of formula $-NR^2$ (where $R^2$ is hydrogen or an alkyl group and in the case of alkyl, it may form a ring jointed with $R^1$), and Y represents acetoxy group or a group of formula $-SR^3$ (where $R^3$ is a nitrogen-containing heterocyclic group), or a pharmaceutically acceptable salt thereof, is found to have a broad antimicrobial spectrum and, in particular, effective against gram-negative bacteria including *Escherichia coli, Klebsiella pneumoniae, Proteus vulgaris, Proteus morganii*, as well as gram positive ones. Thus, these compounds may be used for antimicrobial agents in therapeutical purposes.

20 Claims, No Drawings

CEPHALOSPORIN DERIVATIVES

This is a division of application Ser. No. 534,782, filed Dec. 20, 1974 now U.S. Pat. No. 4,080,498.

This invention relates to novel cephalosporin derivatives having novel 7-acyl groups and preparations thereof. More particularly, this invention relates to 7-[2-(2-exo-substituted-4-thiazolin-4-yl)acetamido]cephalosporin derivatives of the formula:

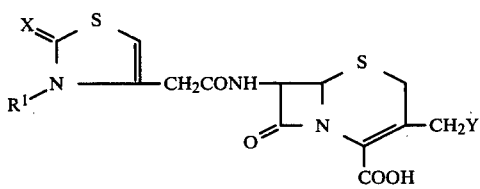

wherein $R^1$ is hydrogen atom or an alkyl group; X is oxygen or sulfur atom or a group of formula $NR^2$ (where $R^2$ is hydrogen or alkyl group and in the case of alkyl, it may form a ring jointed with $R^1$), Y is an acetoxy group or a group of formula $SR^3$ (where $R^3$ is a nitrogen-containing heterocyclic group), or a pharmaceutically acceptable salt thereof and also relates to processes for producing the same.

Heretofore, studies on synthetic cephalosporin derivatives have been directed to the conversion of 7-aminocephalosporanic acid to various acyl derivatives at the 7-position or to derivatives at the 3-acetoxy group in order to synthesize compounds having either a broad antibacterial spectrum or a specific antibacterial spectrum. However, these well-known cephalosporin derivatives are not yet satisfactory in antimicrobial activities against a wide variety of microorganisms. Hence, a compound has been sought after which has a broad or antimicrobial spectrum and is effective even at a lower concentration.

It has now been found that novel cephalosporin derivatives represented by the above formula [I] have broader antimicrobial spectra as compared with those of known cephalosporins. For example, the cephalosporin derivatives [I] are desirable cephalosporin antibiotics, having a strong and broad antimicrobial spectrum especially against such gram-negative bacteria as *Escherichia coli, Klebsiella pneumoniae, Proteus vulgaris* and *Proteus morganii,* showing greater inhibitory activity in comparison with known cephalosporins.

Referring, now, to the above formula [I], $R^1$ means hydrogen, or an alkyl group such as methyl, ethyl, or the like. X represents oxygen, sulfur or a group denoted by either $NR^2$, where $R^2$ stands for a hydrogen or an alkyl group such as those mentioned above by way of example and, in the case of an alkyl, it may constitute a ring along with $R^1$. Y stands for acetoxy group or a group denoted by formula $—SR^3$. $R^3$ stands for a nitrogen-containing heterocyclic group containing not less than one nitrogen which may be in the oxide form or, in addition to nitrogen or nitrogens, such others as oxygen or/and sulfur. The nitrogen-containing heterocyclic group desirably has one to four hetero atoms in its heterocyclic ring and the ring may be 5 or 6 membered one. As such nitrogen-containing heterocyclic group, there may be mentioned, among others, pyridyl, N-oxido-pyridyl, pyrimidyl, pyridazinyl, N-oxido-pyridazinyl, pyrazolyl, diazolyl, thiazolyl, 1,2,3-thiadiazolyl, 1,2,4-thiadiazolyl, 1,3,4-thiadiazolyl, 1,2,5-thiadiazolyl, 1,2,3-oxadiazolyl, 1,2,4-oxadiazolyl, 1,3,4-oxadiazolyl, 1,2,5-oxadiazolyl, 1,2,3-triazolyl, 1,2,4-triazolyl, 1H-tetrazolyl, 2H-tetrazolyl and others. Each of these nitrogen-containing heterocyclic groups may be further substituted and, as the substituents, there may be mentioned monovalent group, for example, lower alkyls such as methyl, ethyl, trifluoromethyl, etc., lower alkoxyls such as methoxy, ethoxy, etc., halogens such as chlorine, bromine, etc., amino, mercapto, hydroxyl, carbamoyl, or carboxyl group, etc. or a substituted lower alkyl group, a substituted mercapto group, or a mono- or di-substituted amino group, etc. The substituents in the substituted lower alkyl group may be hydroxyl, mercapto, amino, morpholino, carboxyl, sulfo, carbamoyl, alkoxycarbonyl, mono-, di- or tri-lower alkylamino, mono- or di-lower alkylcarbamoyl, alkoxy, alkylthio, alkylsulfonyl, acyloxy, morpholinocarbonyl group, etc., wherein the acyloxy group is exemplified by acetoxy, propionyloxy, valeryloxy, caproyloxy, benzoyloxy, phenylacetoxy, etc., the alkoxy group by methoxy, ethoxy, propoxy, butoxy, isobutoxy, hexyloxy, octyloxy, decyloxy, dodecyloxy, etc., and others are the same meaning as hereinbefore described. The substituent of the substituted mercapto group may be a lower alkyl group or a substituted lower alkyl group above mentioned. The substituents of the mono- or di-substituted amino group may be a lower alkyl group, an alkoxycarbonyl, an acyl, carbamoyl, a lower alkylcarbamoyl, or a substituted lower alkyl group mentioned above.

Specifically, use may be made of, for example, a substituted lower alkyl group such as carboxymethyl, carbamoylmethyl, an N-lower alkylcarbamoylmethyl (e.g. N,N-dimethylcarbamoylmethyl), a hydroxy-lower alkyl (e.g. hydroxymethyl, 2-hydroxyethyl), an acyloxy-lower alkyl (e.g. acetoxymethyl, 2-acetoxyethyl), an alkoxycarbonylmethyl (e.g. methoxycarbonylmethyl, hexyloxycarbonylmethyl, octyloxycarbonylmethyl), methylthiomethyl, methylsulfonylmethyl, an N-lower alkylamino-lower alkyl (e.g. N,N-dimethylaminomethyl, N,N-dimethylaminoethyl, N,N,N-trimethylammoniumethyl), morpholinomethyl, etc., mono- or di-substituted amino groups such as a lower alkylamino (e.g. methylamino), a sulfo-lower alkylamino (e.g. 2-sulfo-ethylamino), a hydroxy-lower alkylamino (e.g. hydroxyethylamino), a lower alkylamino-lower alkylamino (e.g. 2-dimethylamino-ethylamino, 2-trimethylammoniumethylamino), an acylamino (e.g. acetylamino, 2-dimethylaminoacetylamino, 2-trimethylammoniumacetylamino), a lower alkoxycarbonylamino (e.g. methoxycarbonylamino), etc., a substituted mercapto group such as methylthio, 2-hydroxyethylthio, a 2-acyloxyethylthio (e.g. 2-acetoxyethylthio, 2-phenylacetoxyethylthio, 2-caproyloxyethylthio), carboxymethylthio, an alkoxycarbonylmethylthio (e.g. methoxycarbonylmethylthio, hexyloxycarbonylmethylthio), carbamoylmethylthio, an N-lower alkylcarbamoylmethylthio (e.g. N,N-dimethylcarbamoylmethylthio), acetylmethylthio, an N-lower alkylamino-lower alkylthio (.e.g. 2-N,N-dimethylamino-ethylthio, 2-N,N,N-trimethylammonium-ethylthio), morpholinocarbonylmethylthio, 2-sulfoethylthio, etc.

The 7-2-(2-exo-substituted-4-thiazolin-4-yl)acetamido]cephalosporin derivatives [I] of this invention may be used with its 4-carboxyl group being free or after being made into a pharmaceutically acceptable salt with a nontoxic cation such as sodium, potassium or the like; a basic amino acid such as arginine, ornithine, lysine, histidine or the like; or a polyhydroxyalkylamine such as N-methylglucamine, diethanolamine, triethanolamine, tris-hydroxymethylaminomethane or the like. The compounds [I] may also be used after it has been converted to a biologically active ester derivative by esterification of its 4-carboxyl group, said ester derivatives being conducive to, for instance, an increased blood level or/and a longer duration of activity. As the ester residues of use for this purpose, there may be mentioned, for example, alkoxylmethyl and α-alkoxyethyl and other α-alkoxy-α-substituted methyl groups, e.g. methoxymethyl, ethoxymethyl, isopropoxymethyl, α-methoxyethyl, α-ethoxyethyl, etc.; alkylthiomethyl groups, e.g. methylthiomethyl, ethylthiomethyl, isopropylthiomethyl, etc.; and acyloxymethyl and α-acyloxy-α-substituted methyl groups, e.g. pivaloyloxymethyl, α-acetoxybutyl, etc.

The cephalosporin derivatives [I] of the present invention may be prepared by a variety of means. The following are examples of them.

Process 1.

A process for producing cephalosporin derivatives of the formula [I], in which a compound of the formula;

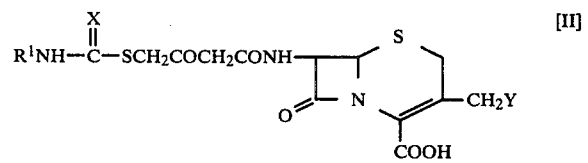

wherein each of the symbols has the same meaning as above, or a salt or an ester thereof, is subjected to ring closure reaction with elimination of water.

Process 2.

A process for producing cephalosporin derivatives of the formula [I], in which a compound of the formula;

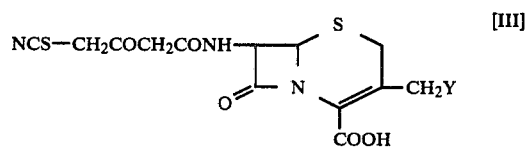

wherein Y has the same meaning as above, or a salt or an ester thereof, is allowed to react with a compound of the formula;

wherein X has the same meaning as above, to obtain a compound of the formula;

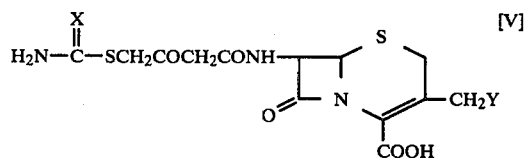

wherein each of the symbols has the same meaning as above, and thus obtained compound [V] is subjected to ring closure reaction with elimination of water.

Process 3.

A process for producing cephalosporin derivatives [I], in which a compound of the formula;

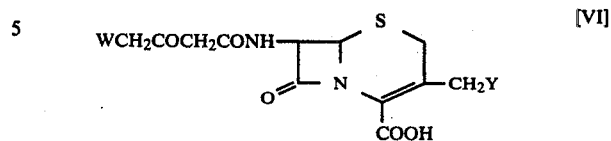

wherein W is a halogen and other symbol has the same meaning given hereinbefore, or a salt or an ester thereof, is allowed to react with a compound of the formula;

wherein each of the symbols has the meaning given hereinbefore, or a salt thereof, to obtain a compound of the formula [II] and thus obtained compound [II] is subjected to ring closure reaction with elimination of water.

Process 4.

A process for producing cephalosporin derivative of the formula;

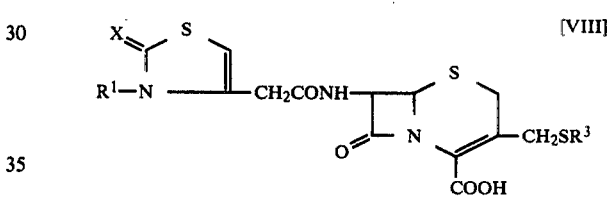

wherein each of the symbols has the same meaning as above, in which a compound of the formula;

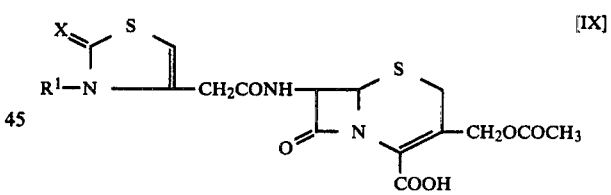

wherein each of the symbols has the same meaning given hereinbefore, or a salt thereof, is allowed to react with a compound of the formula;

wherein $R^3$ is the same meaning as above.

Process 5.

A process for producing cephalosporin derivatives of the formula;

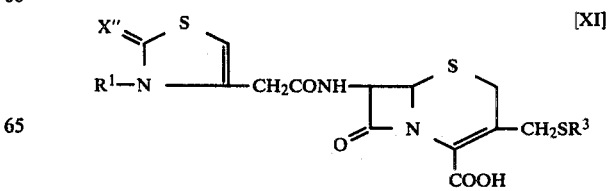

wherein X" represents oxygen, sulfur or an imino group which may be protected, and each of other symbols has the same meaning as above, in which a compound of the formula;

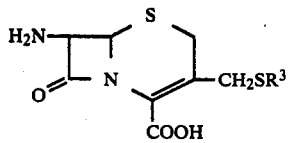

[XII]

wherein R³ has the same meaning as above, or a salt or an ester thereof, is allowed to react with a compound of the formula;

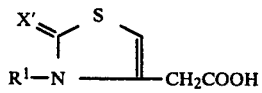

[XIII]

wherein X' represents oxygen, sulfur or a protected imino group and R¹ has the same meaning as above, or reactive derivative thereof, and, if desired, the protective group of the imino group is further removed from the product.

The followings are a detailed explanation of these processes 1 to 5.

Process 1

The ring closure reaction of the compounds [II] into the objective compounds [I] takes place readily in a solvent. As the solvent just mentioned, there may be employed, usually, water, alcohols (e.g. methanol, ethanol, etc.), acetone, acetonitrile, chloroform, dioxane, ethylene chloride, tetrahydrofuran, ethyl acetate, dimethylformamide and dimethylsulfoxide, as well as suitable mixtures of such solvents. The reaction is accelerated by the presence of a Lewis acid or a base which works as a dehydrating catalyst. As said acid, there may be employed any of phosphate buffers of acid pH, hydrochloric acid, phosphoric acid and sulfuric acid, as well as their acid alkali metal salts, and other inorganic acids and organic acids such as acetic acid and lactic acid. As the base, there may usually be employed any of such inorganic or organic bases as basic phosphate buffers, alkali metal hydroxides (e.g. sodium hydroxide, potassium hydroxide, etc.), alkali metal hydrogen carbonates (e.g. sodium hydrogen carbonate, potassium hydrogen carbonate, etc.), ammonia, N,N-dicyclohexylamine, triethylamine, pyridine, ammonia and N,N-dimethylaniline. The starting compound [II] is subjected to the reaction as the free acid or as an alkali metal salt, e.g. the salt of sodium, potassium or the like or as an easily cleavable ester such as the trimethylsilyl ester, methoxymethyl ester, 2-methylsulfonylethyl ester, p-nitrobenzyl ester, 2,2,2-trichloroethyl ester, trityl ester or the like. The reaction usually proceeds satisfactorily enough at the temperature from about −70° C. to about room temperature, although it may be conducted under heating or cooling, if necessary. The reaction is carried out under stationary conditions for a few to tens of hours, whereby the ring closure product [I] is formed. When a buffer solution is selected as the solvent, the conversion to [I] may take place to a satisfactory extent merely by dissolving [II] in the buffer and allowing the solution to stand, for the buffer contains the above-mentioned acid or base as one of its components.

Whether an acid is (or acid conditions are) required or a base is (or basic conditions are) required for this reaction can be easily ascertained, for example by mixing [II] with said acid or base in a solvent in a small scale and examining the resultant by thin-layer chromatogram, for the starting compound [II] and desired product [I] can be easily differentiated by thin-layer chromatography. In this way, the selective necessity of an acid or a base and other required reaction conditions can be selected with accuracy.

It should also be understood that some of compounds [II] are so ready to cyclize that they may cyclize under the above-described reaction conditions employed in the production of themselves. In such cases, it is unnecessary to isolate [II] but [I] is formed under the very conditions of manufacture of the starting material. That is to say, the compounds [II] are so likely to cyclize into [I] that even during the preparative reactions of themselves, e.g. the first step of Process 2 and 3, they gradually are transformed into [I]. Therefore, it is practical to conduct the present reaction in combination with the first step of Process 2 and 3.

The 7-[2-(2-exo-substituted-4-thiazolin-4-yl)acetamido]-cephalosporin derivative [I] thus resulted can be isolated and purified by procedures which are known per se, such as solvent extraction, pH adjustment, phasic transfer, distillation, crystallization, recrystallization, chromatography, de-esterification, etc.

Process 2

The 7-(4-thiocyano-3-oxobutyrylamido)-cephalosporin derivative [III] is reacted with water, hydrogen sulfide or an amine of the formula H₂X (X is as hereinbefore defined) [IV]. The mode of presence of [III], the types of solvent, acid and base, the procedure for selecting the conditions of reaction, the reaction conditions and the procedure for isolating the product may be similar to those described above in connection with the conversion of [II] to [I]. Practically, the compounds [V] generated are, without isolation, in situ, transformed into [I] spontaneously or, if desired, by the treatment described in the above Process 1.

Process 3

The halogen W in formula [VI] may usually be chlorine or bromine. As preferred examples of said thiol compound [VII], there may be mentioned thiourea, alkylated or acylated thiourea, N,N'-ethylenethiourea, ammonium dithiocarbamate, ammonium thiocarbamate, etc. Referring to the reaction of [VI] with [VII], the former compound [VI] is usually subjected to the reaction in its free form and the latter [VII] is used ordinarily in its free form or in the form of a salt at the thiol function thereof with an alkali metal, e.g. lithium, sodium or potassium, or ammonium. The reaction is ordinarily carried out by admixing equimolar proportions of the two materials together with 1 to 2 molecular equivalents of a base in the presence of a solvent. As solvents suited for this reaction, there may be mentioned water, methanol, ethanol, acetone, dioxane, acetonitrile, chloroform, ethylene chloride, tetrahydrofuran, ethyl acetate, dimethylformamide, dimethylacetamide and other common organic solvents which will not interfere with the reaction. Of these solvents, hydrophilic solvents may be used in admixture with water. As the base, there may be mentioned, among others, alkali hydroxides such as sodium hydroxide, potassium hydroxide, etc.; alkali metal carbonates such as sodium carbonate, potassium carbonate, etc.; alkali metal hydrogen carbonates such as sodium hydrogen carbonate, etc.; and organic tertiary amines such as trimethylamine, triethylamine, pyridine, etc. Since the base is intended for the neutralization of the carboxyl group of the cephalosporin and the hydrogen halide that will be liberated in the course of the reaction, it is desirably used in a proportion of about 2 equivalents when the substituted thiol [VII] is employed in its free form or a proportion of about one equivalent when the same [VII] is employed in the form of an alkali metal salt, for instance. There is no particular limitation upon the reaction temperature, although the reaction ordinarily is desirably conducted under cooling, e.g. about $-30°$ C. to the room temperature. The reaction generally proceeds fast, going to conclusion within 10 minutes, although at times it takes more than about half an hour to carry through the reaction.

The hydrogen halides or their salts liberated during the reaction of compounds [VI] with [VII] may be served as efficient dehydrating catalyst for the ring closure of the resulted compounds [II] and, therefore, the second step of the present Process 3 proceeds generally without any additional treatments. Alternatively, the intermediates [II] may be isolated and purified by per se known process and subjected to the ring closure reaction of the Process 1.

Process 4

The 7-[2-(2-exo-substituted-4-thiazolin-4-yl)acetamido]-3-acetoxymethyl-cephalosporin derivative [IX], which is among the compounds obtained according to the above-described Processes 1 to 3, can be further reacted with a nitrogen-containing heterocyclic thiol of formula $R^3SH$ [X] to obtain a 7-[2-(2-exo-substituted-4-thiazolin-4-yl)acetamido]-cephalosporin derivative [VIII]. The [IX] to be used may be an isolated compound or the reaction mixture of the above-mentioned Processes 1 to 3. The compounds [IX] may be used as a free form or the salt of the base used in the procedure described above, examples of which are salts with alkali metals such as sodium, potassium, etc. or organic amines such as trimethylamine, triethylamine, etc. The nitrogen-containing heterocyclic thiol [X] to be employed is subjected to the reaction in its free form or as a salt at its thiol function with an alkali metal such as lithium, sodium, potassium or the like.

This reaction is usually effected by heating at 40° to 80° C. in the neighborhood of neutrality. The reaction is carried out in a solvent, preferred examples of which are water and aqueous solvents such as mixtures of water with highly polar solvents which will not interfere with the reaction, e.g. acetone, tetrahydrofuran, dimethylformamide, methanol, ethanol, dimethylsulfoxide, etc.

When [IX] is used in its free form, it is sometimes desirable to incorporate in the reaction system a base such as sodium hydrogen carbonate, potassium hydrogen carbonate, sodium carbonate, potassium carbonate or the like so as to adjust the pH to neutral. If necessary, a buffer solution may also be employed. The reaction time and other conditions of reaction should be determined with reference to such factors as the types of starting materials and solvent, temperature, etc. The cephalosporin derivatives [VIII] thus resulted can be isolated and purified by conventional procedures similar to those hereinbefore described.

Process 5

In conducting this reaction, the 4-carboxyl group of 7-amino compound [XII] may be in any forms that can be easily converted into a free carboxyl group by treatment with an alkali, acid or enzyme or by reduction, or in the form of an ester which is active in vivo. Thus, the corresponding salts with alkali metals, alkaline earth metals, organic amines, etc., e.g. sodium, potassium, magnesium, calcium, aluminum, triethylamine, etc., and the corresponding esters with $\beta$-methylsulfonylethyl, trimethylsilyl, dimethylsilenyl, benzhydryl, $\beta,\beta,\beta$-trichloroethyl, phenacyl, p-methoxybenzyl, p-nitrobenzyl, methoxymethyl, etc. may be mentioned. The carboxylic acid compound [XIII] can be used in the acylation reaction as the free acid or as the corresponding salt with sodium, potassium, calcium, trimethylamine, pyridine or the like or, further, as reactive derivatives such as acid halide, acid anhydride, mixed acid anhydride, cyclic carboxyanhydride, active amide, ester, etc., among which the acid chloride, alkyl carbonate anhydride, aliphatic carboxylic acid anhydride, acid azolide, etc. are more commonly employed. As the active ester, there may be used, for example, P-nitrophenyl ester, 2,4-dinitrophenyl ester, pentachlorophenyl ester, N-hydroxysuccinoimidoyl ester, N-hydroxyphthalimidoyl ester, etc. As the mixed acid anhydride, there may be used, for example, anhydride with carbonate monoesters (e.g. monomethyl carbonate, mono-iso-butyl carbonate, etc.) or halogen substituted or non-substituted lower alkanoic acids (e.g. pivalic acid, trichloroacetic acid, etc.). When the symbol X represents imino group, it is desirable that the imino group is protected prior to the acylation with an easily removable protective group such as proton, t-butoxycarbonyl or trichloroethoxy carbonyl group, etc. The acylation reaction can be conducted advantageously in a solvent. As said solvent, use may be made of the common solvents and their mixtures unless such solvents do not interfere with the present reaction. There may be mentioned, therefore, such solvents as water, acetone, tetrahydrofuran, dioxane, acetonitrile, chloroform, dichloromethane, dichloroethylene, pyridine, dimethylaniline, dimethylsulfoxide, etc. While the reaction temperature is virtually optional, the reaction usually is carried out under cooling or at room temperature. When the carboxylic acid compound [XIII] is employed in the form of free acid or salt, a suitable condensing agent is used together. The condensing agent includes, among others, di-substituted carbodiimides (e.g. N,N'-dicyclohexylcarbodiimide), azolide compounds (e.g. N,N'-carbonylimidazole, N,N'-thionyldiimidazole, etc.), and such dehydrating agents as N-ethoxycarbonyl-2-ethoxy-1,2-dihydroquinoline, phosphorus oxychloride, alkoxyacetylene, etc. It appears that when such a condensing agent is employed, the reaction proceeds via a reactive intermediate at the carboxyl group. When the reaction proceeds with the liberation of acid, a base is preferably added to the reaction system to neutralize the acid. As the bases suitable for this purpose, there may be commonly used aliphatic, aromatic or heterocyclic nitrogen-containing bases or alkali metal carbonates and bicarbonates such as, for example, triethylamine, N,N-dimethylaniline, N-ethylmorpholine, pyridine, collidine, 2,6-lutidine, sodium carbonate, potassium carbonate, sodium hydrogen carbonate, potassium hydrogen carbonate and the like. When a dehydrating reagent is employed, it is, of course, preferable to exclude water from the solvent. It is sometimes desirable to carry out the method in an inert gas such as nitrogen gas to the exclusion of moisture.

The compound [XI] resulted is, if necessary, subjected to a procedure for removal of the protective group, and then to an usual work-up for isolation and purification similar to that hereinbefore mentioned. When the imino group of the starting compound [XII] is protected with a proton delivered from an acid, a free imino compound [XIII] is obtained only by shifting the pH to alkaline side in the purification procedure. When the imino group is protected with an acyl group, a conventional de-acylation procedure for the group is employed, e.g. acid treatment for formyl, amyloxycarbonyl, t-butoxycarbonyl group, etc., reduction for 2,2,2-trichloroethoxycarbonyl, benzyloxycarbonyl, p-nitrobenzyloxycarbonyl group, etc., an alkali treatment for 2-methylsulfonyl-ethoxycarbonyl group, etc.

Preparations of the starting materials for use in Process 1 to 5

The 3-nitrogen-containing heterocyclic thiomethyl compounds [III], [VI] and [XII] are prepared by the reaction formulated below;

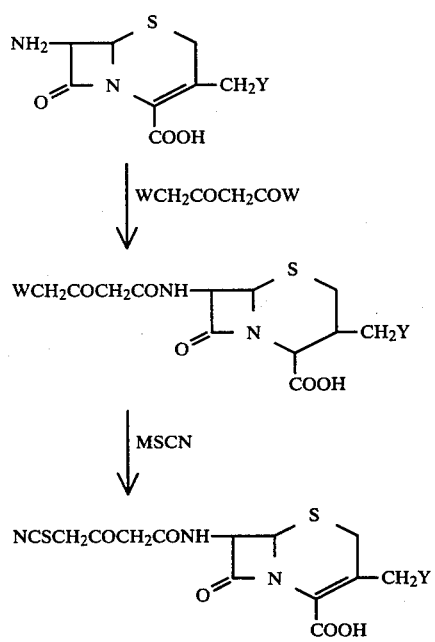

wherein M represents an alkali metal and each other symbols is the same meaning as above.

The nitrogen-containing heterocyclic thiol compounds [X] include novel compounds which are not described themselves in the literature and such novel compounds are prepared by per se known heterocyclic synthesis described in e.g. Chapter 5 of Heterocyclic Chemistry (A. R. Katritzky and J. M. Logwski, published by John Wiley & Sons . . . , 1960) or by a per se known modification reactions on easily or commercially available nitrogen-containing heterocyclic thiols.

The amino compounds [XII] may be prepared by deacylating the reaction product of cephalosporin C and a nitrogen-containing heterocyclic thiol [X], or by reacting 7-protected aminocephalosporanic acid with a nitrogen-containing heterocyclic thiol [X] and removing the protecting group from the reaction product.

Structure and Nomenclature

When $R^1$ is hydrogen, the compounds [I] may take the two tautomeric forms as formulated below:

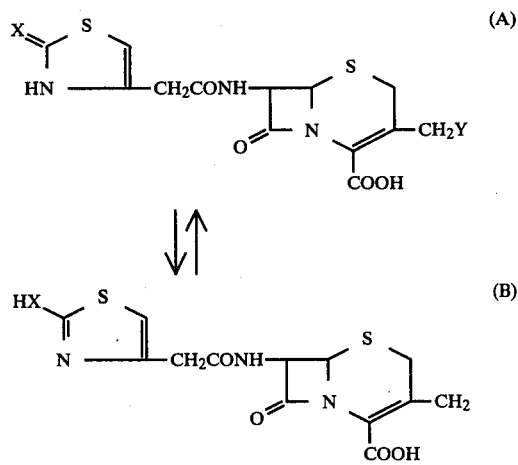

wherein each of the symbols used has the same meaning given hereinbefore. The actual physical data of such compounds indicate that, when X is oxygen or sulfur, the compounds [I] exist exclusively in thiazoline form (A), whereas, when X is imino group, they exist in an equilibrium state between the two forms, even if the equilibrium lies to the left (i.e. towards compound A) by the contribution of the intramolecular association depicted below.

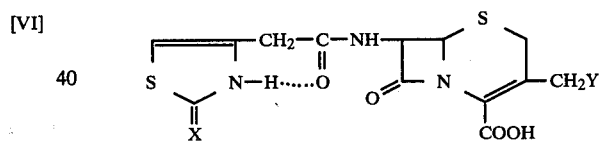

However, the nomenclature of the compounds [I] in the present invention is enforced, when $R^1$ is hydrogen or an alkyl and X is oxygen or sulfur, by the thiazoline form (A) and, when $R^1$ is hydrogen and X is imino group, by the thiazole form (B) in conformity with the nomenclature of similar compounds adopted by Chemical Abstracts. The tautomeric isomers, however, are all included within the scope of this invention.

The 7-[2-(2-exo-substituted-4-thiazolin-4-yl)acetamido]-cephalosporin derivatives [I] thus obtained have a broad and potent antimicrobial spectrum, showing activity against gram-negative and gram-positive bacteria, and especially against such gram-negative bacteria as *Escherichia coli, Klebsiella Pneumoniae, Proteus vulgaris* and *Proteus morganii*, these compounds [I] are more potent than the hithertoknown cephalosporins. Thus, these compounds yield excellent therapeutic effects in the treatment of infections with these bacteria in human beings and animals.

Like the known cephalosporins, the contemplated compounds [I] of this invention can each be administered orally or parenterally in the form of powders or in such exemplary forms as solutions or suspensions in admixture with a physiologically acceptable vehicle or excipient in accordance with the established pharmaceutical procedure.

Specifically, in the treatment of various human diseases caused by the above-mentioned bacteria, suppurative diseases, respiratory-organ infections, bile-duct infections, infections of the intestines, urinary-tract infections and obsteric and gynecologic infections, the contemplated compounds of this invention, such as sodium 7-[2-(2-aminothiazol-4-yl)acetamido]-3-(1,3,4-thiadiazol-2-yl)thiomethyl-3-cephem-4-carboxylate, sodium 7-[2-(2-aminothiazol-4-yl)acetamido]-3-(1-methyltetrazol-5-yl)thiomethyl-3-cephem-4-carboxylate, sodium 7-[2-(2-oxo-4-thiazolin-4-yl)acetamido]-3-[2-(2-acetoxyethylthio)-1,3,4-thiadiazol-5-yl]thiomethyl-3-cephem-4-carboxylate, disodium 7-[2-(2-aminothiazol-4-yl)acetamido]-3-(2-carboxymethyl-1,3,4-thiadiazol-5-yl)thiomethyl-3-cephem-4-carboxylate, sodium 7-[2-(2-aminothiazol-4-yl)acetamido]-3-(2-carbamoylmethyl-1,3,4-thiadiazol-5-yl)thiomethyl-3-cephem-4-carboxylate, sodium 7-[2-(2-aminothiazol-4-yl)acetamido]-3-(2-carbamoylmethylthio-1,3,4-thiadiazol-5-yl)thiomethyl-3-cephem-4-carboxylate, are each desirably administered parenterally (non-orally) at a daily dose level of about 5 to 20 mg./kg. body weight in 3 to 4 divided doses per day.

The present invention is illustrated in further detail below with reference to examples, but it is to be understood that the examples are solely for the purpose of illustration and not to be construed as limitations of the invention, and that many variations may be resorted to without departing from the spirit and scope of the invention. In this specification, "g.", "mg.", "kg.", "ml.", "cm.", "ppm", "Hz", "MHz", "mol", "m mol", "meg", "Calcd.", "DMSO", "nm" and "decomp." are abbreviations of "gram", "milligram", "kilogram", "milliliter", "centimeter", "part per million", "Herz", "mega Herz", "Mole", "milli-Mole", "microgram", "Calculated", "dimethylsulfoxide", "Nano meter", and "decomposed", respectively. Resins named "Amberlite" are products manufactured by Rohm & Hars Co. in U.S.A. All the temperatures are uncorrected and the percentages are all on the weight basis except specifically defined. The NMR spectra given therein were measured using a Varian Model HA 100 (100 MHz) or T60 (60 MHz) spectrometer with tetramethylsilane as the internal or external reference and all $\delta$ values are in ppm. The symbol s stands for a singlet, d a doublet, t a triplet, q a quartet, m a multiplet, and J a coupling constant.

REFERENCE EXAMPLE 1

Production of (2-oxo-4-thiazolin-4-yl)acetic acid (1) Ethyl (2-oxo-4-thiazolin-4-yl)acetate A mixture of 2.1 g. of thiocarbamic acid —O— methyl ester, 1 g. of ethyl 4-bromoacetoacetic acid and 1 ml. of dimethylacetamide is allowed to stand at room temperature for 16 hours. To this mixture is added 40 ml. of ethyl acetate. The mixture is washed with water (40 ml.×3) and dehydrated. The solvent is distilled off and the residue is further concentrated to dryness to give crystals. The crystalline mass is triturated with ether and filtered under suction. The procedure yields the above-indicated compound.

Yield 1.07 g. (57%).
m.p. 106°–110° C.
IR(cm$^{-1}$, KBr): 1745, 1655.
NMR(60 MHz, d$_6$-DMSO, $\delta$): 1.23(t, J7 Hz, CH$_3$CH$_2$—), 3.40(s, CH$_2$CO), 4.17(q, J7 Hz, CH$_3$CH$_2$), 6.05(s, thiazoline 5-H), 11.05(broad s, thiazoline NH).

(2) (2-oxo-4-thiazolin-4-yl)acetic acid

In a mixture of 5 ml. of 1 N aqueous sodium hydroxide and 5 ml. of tetrahydrofuran are dissolved 0.83 g. of the crystals obtained in the above procedure (1), and the solution is allowed to stand in a refrigerator for 3 days. The tetrahydrofuran is distilled off under reduced pressure and the residue is adjusted to pH 2.5 with concentrated phosphoric acid and extracted with a 1:1 mixture of ethyl acetate and tetrahydrofuran (5 ml.×2). The organic layers are pooled, dehydrated and concentrated to dryness under reduced pressure. Ether is added to the residue and the inner wall of the vessel is rubbed, whereupon crystals separate out. These crystals are recovered by filtration. The procedure yields 0.39 g. (55%) of the above-indicated compound.

m.p. 112° C.(decomp.).
IR(cm$^{-1}$, KBr): 1725.
NMR(60 MHz, d$_6$-DMSO, $\delta$): 3.37(s, CH$_2$CO), 6.08(s, thiazoline 5-H), 11.06(broad s, thiazoline NH).

REFERENCE EXAMPLE 2

Production of (2-thioxo-4-thiazolin-4-yl)acetic acid (1) Ethyl (2-thioxo-4-thiazolin-4-yl)acetate In 25 ml. of water is dissolved 6.2 g. of ammonium dithiocarbamate and, then, 11.8 g. of ethyl 4-bromoacetoacetate is added to the solution. The heat generated thereby brings the solution temperature to about 50° C. This mixture is stirred at room temperature for a day and, then, at 90° to 100° C. for 2 hours. After cooling, the reaction mixture is extracted with ethyl acetate. The ethyl acetate layer is washed with a saturated aqueous solution of sodium chloride and dried. The solvent is then distilled off and the residue is triturated with the addition of ether, whereupon crystals separate out. The crystals are recovered by filtration and washed with ether. The procedure yields 2.5 g. (22%) of the above-indicated compound.

IR(cm$^{-1}$, KBr): 1732.
NMR(60 MHz, d$_6$-DMSO+CDCl$_3$, $\delta$): 1.27(t, J7 Hz, CH$_3$CH$_2$), 3.57(s, CH$_2$CO), 4.19(q, J7 Hz, CH$_3$CH$_2$), 6.50(s, thiazoline 5-H)), 12.89(broad s, thiazoline NH).

(2) (2-thioxo-4-thiazolin-4-yl)acetic acid

In 19.24 ml. of a 1 N aqueous solution of sodium hydroxide is dissolved 1.68 g. of the crystals obtained in procedure (1) and the solution is stirred at room temperature for 4 hours. This reaction mixture is brought to pH 2 with concentrated phosphoric acid and extracted with ethyl acetate (60 ml.×4). The extracts are pooled, dehydrated and concentrated under reduced pressure. Ether is added to the residue and the mixture is allowed to stand, whereupon crystals separated. The crystals are recovered by filtration under suction. The described procedure yields 1.42 g. (98%) of the above-indicated compound.

m.p. 155°–157° C.
IR(cm$^{-1}$, KBr): 1697.
NMR(60 MHz, d$_6$-DMSO, $\delta$): 3.52(s, CH$_2$CO), 6.63(s, thiazoline 5-H), 8.0(broad s, COOH), 13.0 (broad s, thiazoline NH).

EXAMPLE 1

Production of 7-[2-(2-oxo-4-thiazolin-4-yl)acetamido]-3-acetoxymethyl-3-cephem-4-carboxylic acid In 5 ml. of a phosphate buffer solution of pH 6.4 are dissolved 0.413 g. of 7-(4-thiocyano-3-oxobutyrylamido)-3-acetoxymethyl-3-cephem-4-carboxylic acid and 0.084 g. of sodium hydrogen carbonate and the solution is allowed to stand at room temperature for 48 hours. This mixed solution is adjusted to pH 3.0 with a 50% aqueous solution of phosphoric acid, then saturated with sodium chloride and extracted with ethyl acetate (3×10 ml.). The ethyl acetate solution is washed with an aqueous solution of sodium chloride, dehydrated and concentrated. Following the addition of ether, the concentrate is allowed to stand, whereupon crystals emerge. These crystals are recovered by filtration under suction. The described procedure gives the above-indicated compound. Yield 0.18 grams.

Melting point: 180° C.

IR(cm$^{-1}$, KBr): 1775, 1715, 1665.

UVλmax(ε in 1% aqueous NaHCO$_3$): 248 nm(1.14×10$^4$).

NMR (δ in d$_6$-DMSO): 2.01(s, CH$_3$CO), 3.33(s, CH$_2$CO), 3.43 & 3.66(ABq, J18 Hz, 2—CH$_2$), 4.69 & 5.00 (ABq, J13 Hz, 3—CH$_2$), 5.08(d, J4.5 Hz, 6-H), 5.69(dd, J4.5 & 8.0 Hz, 7—H), 6.00(s, thiazoline 5-H), 8.96(d, J8.0 Hz, CONH).

Elemental analysis: Calcd. for C$_{15}$H$_{15}$N$_3$O$_7$S$_2$: C, 43.58; H, 3.66; N, 10.16. Found: C, 43.37; H, 3.48; N, 9.77.

EXAMPLE 2

Production of 7-[2-(2-oxo-4-thiazolin-4-yl)acetamido]-3-(1-methyltetrazol-5-yl)thiomethyl-3-cephem-4-carboxylic acid In 27 ml. of a phosphate buffer solution of pH 6.4 are dissolved 0.67 g. of 7-(4-thiocyano-3-oxobutyrylamido)-3-acetoxymethyl-3-cephem-4-carboxylic acid and 0.116 g. of sodium hydrogen carbonate and the resulting solution is allowed to stand overnight. To this mixed solution is added 0.168 g. of 1-methyltetrazole-5-thiol and the mixture is stirred at 56°–59° C. for 8 hours. After cooling, the reaction mixture is adjusted to pH 3 with a 50% aqueous solution of phosphoric acid and extracted with ethyl acetate (3×20 ml.). The ethyl acetate solution is washed with water, dehydrated, concentrated and allowed to stand. The resulting crystals are recovered by filtration under suction. The described procedure gives the above-indicated compound. This product includes one mole of ethyl acetate as the solvent of crystallization.

Yield 0.25 grams. Melting point: 107° C.(decomp.)

IR(cm$^{-1}$, KBr): 1785, 1730, 1660.

UVλmax(ε in ethanol): 244 nm(1.22×10$^4$).

NMR(δ in d$_6$-DMSO): 3.34(s, CH$_2$CO), 3.70(m,2-CH$_2$), 3.92(s, tetrazole CH$_3$), 4.30(m, 3-CH$_2$), 5.07(d, J5 Hz, 6-H), 5.68(dd, J5 & 8 Hz, 7-H), 6.01(s, thiazoline 5-H), 8.98(d, J8 Hz, CONH).

Elemental analysis: Calcd. for C$_{15}$H$_{15}$N$_7$O$_5$S$_3$·CH$_3$COOC$_2$H$_5$: C, 40.92; H, 4.16; N, 17.57. Found: C, 40.51; H, 4.00; N, 16.61.

| Strain of microorganism | Antibacterial spectra (mcg/ml., agar dilution method) | | |
|---|---|---|---|
| | Product of this example | Cephaloridine | Cephazolin |
| S. aureus 209P | <0.78 | 0.05 | 0.1 |
| S. aureus 1840 | <0.78 | 0.39 | 1.56 |
| E. coli NIHJ JC-2 | <0.78 | 6.25 | 1.56 |
| E. coli 0-111 | <0.78 | 3.125 | 1.56 |
| K. pneumoniae DT | <0.78 | 3.125 | 1.56 |

EXAMPLE 3

Production of 7-[2-(2-oxo-4-thiazolin-4-yl)acetamido]-3-(1-methyltetrazol-5-yl)thiomethyl-3-cephem-4-carboxylic acid In 5 ml. of a phosphate buffer solution of pH 6.4 are dissolved 0.47 g. of 7-(4-thiocyano-3-oxobutyrylamido)-3-(1-methyltetrazol-5-yl)thiomethyl-3-cephem-4-carboxylic acid and 0.084 g. of sodium hydrogen carbonate and the solution is allowed to stand at room temperature for 48 hours. This mixed solution is adjusted to pH 2 with a 50% aqueous solution of phosphoric acid and extracted with ethyl acetate (3×20 ml.). The ethyl acetate extracts are pooled, washed with water, dehydrated, concentrated and allowed to stand, whereupon crystals are obtained. These crystals are recovered by filtration. The described procedure gives the above-indicated compound which is in good agreement with the product according to Example 2 in IR and NMR spectra. Yield 0.28 g.

EXAMPLE 4

Production of 7-[2-(2-oxo-4-thiazolin-4-yl)acetamido]-3-(1,3,4-thiadiazol-2-yl)thiomethyl-3-cephem-4-carboxylic acid In a mixture of 20 ml. of a phosphate buffer solution of pH 6.4 and 2.5 ml. of tetrahydrofuran are dissolved 0.487 g. of 7-(4-thiocyano-3-oxobutyrylamido)-3-acetoxymethyl-3-cephem-4-carboxylic acid and 0.084 g. of sodium hydrogen carbonate, and the resulting solution is allowed to stand overnight. In this mixed solution are dissolved 0.13 g. of 1,3,4-thiadiazole-2-thiol and 0.084 g. of sodium hydrogen carbonate and the solution is stirred under heating at 58° C. for 16 hours. After cooling, the solution is rendered acid with a 50% aqueous solution of phosphoric acid, treated with activated carbon and extracted with ethyl acetate (2×20 ml.). The ethyl acetate extract is washed with water, dehydrated, concentrated under reduced pressure and allowed to stand. The resulting crystals are recovered by filtration under suction. The described procedure gives the above-indicated compound. This product includes one mole each of ethyl acetate and water as solvents of crystallization. Yield 0.1 g. Melting point: 122°–140° C.(decomp.).

IR(cm$^{-1}$, KBr): 1780, 1650, 1535.

NMR(δ in d$_6$-DMSO): 3.33(s, CH$_2$CO), 3.69(m, 2-CH$_2$), 4.29 & 4.57(ABq, J14 Hz, 3-CH$_2$), 5.07(d, J4.5 Hz, 6-H), 5.68(dd, J4.5 & 8 Hz, 6-H), 5.68(dd, J4.5 & 8 Hz, 7-H), 8.98(d, J8 Hz, CONH), 9.50(s, thiadiazole 5-H).

Elemental analysis: Calcd. for C$_{15}$H$_{13}$N$_5$O$_5$S$_4$·CH$_3$COOC$_2$H$_5$·H$_2$O: C, 39.50; H, 4.01; N, 12.12. Found: C, 39.25; H, 3.15; N, 11.74.

| Strain of microorganism | Antibacterial spectra (mcg/ml., agar dilution method) | | |
|---|---|---|---|
| | Product of this example | Cephaloridine | Cephazolin |
| S. aureus 209P | <0.78 | 0.05 | 0.01 |
| S. aureus 1840 | <0.78 | 0.39 | 1.56 |
| E. coli 0-111 | 1.56 | 3.125 | 1.56 |
| K. pneumoniae DT | 1.56 | 3.125 | 1.56 |

EXAMPLE 5

Production of 7-[2-(2-oxo-4-thiazolin-4-yl)acetamido]-3-(1,3,4-thiadiazol-2-yl)thiomethyl-3-cephem-4-carboxylic acid In 5 ml. of a phosphate buffer solution of pH 6.4 are dissolved 0.47 g. of 7-(4-thiocyano-3-oxobutyrylamido)-3-(1,3,4-thiadiazol-2-yl)thiomethyl-3-cephem-4-carboxylic acid and 0.084 g. of sodium hydrogen carbonate and the solution is allowed to stand at room temperature overnight. This mixed solution is adjusted to pH 3 with a 50% aqueous solution of phosphoric acid and extracted with ethyl acetate (3×20 ml.). The ethyl acetate extract is washed with water, dehydrated, concentrated under reduced pressure and allowed to stand. The resulting crystals are recovered by filtration. The procedure gives the above-indicated compound which is in good agreement with the product according to Example 4 in IR and NMR spectra. Yield 0.23 g.

EXAMPLE 6

Production of 7-[2-(2-oxo-4-thiazolin-4-yl)acetamido]-3-(5-methyl-1,3,4-oxadiazol-2-yl)thiomethyl-3-cephem-4-carboxylic acid In a mixture of 20 ml. of a phosphate buffer solution of pH 6.4 and 2.5 ml. of tetrahydrofuran are dissolved 0.487 g. of 7-(4-thiocyano-3-oxobutyrylamido)-3-acetoxymethyl-3-cephem-4-carboxylic acid and 0.084 g. of sodium hydrogen carbonate and the resulting solution is allowed to stand overnight. In this mixed solution are dissolved 0.13 g. of 5-methyl-1,3,4-oxadiazole-2-thiol and 0.084 g. of sodium hydrogen carbonate, and the solution is stirred under heating at 58° C. for 7 hours. After cooling, the reaction mixture is rendered acid with a 50% aqueous solution of phosphoric acid and extracted with ethyl acetate (2×20 ml.). The ethyl acetate extract is washed with water, dehydrated and concentrated under reduced pressure. The concentrate is allowed to stand and the resulting crystals are recovered by filtration under suction. The procedure gives the above-indicated compound. This product includes a mole each of ethyl acetate and water as solvents of crystallization.

Yield 0.1 g. Melting point: 122°–140°(decomp.).

IR(cm$^{-1}$, KBr): 1784.

NMR($\delta$ in d$_6$-DMSO): 2.44(s, oxadiazole CH$_3$), 3.32(s, CH$_2$CO), 3.54 & 3.78(ABq, J18 Hz, 2-CH$_2$), 4.13 & 4.36(ABq, J14 Hz, 3-CH$_2$), 5.06(d, J4.5 Hz, 6-H), 5.66(m, 7-H), 6.00(s, thiazoline 5-H), 8.98(d, J9 Hz, CONH).

Elemental analysis: Calcd. for C$_{16}$H$_{15}$N$_5$O$_6$S$_3$·CH$_3$COOC$_2$H$_5$·H$_2$O: C, 41.72; H, 4.38; N, 12.17. Found: C, 41.40; H, 3.71; N, 12.04.

EXAMPLE 7

Production of 7-[2-(2-oxo-4-thiazolin-4-yl)acetamido]-3-(5-methyl-1,3,4-oxadiazol-2-yl)thiomethyl-3-cephem-4-carboxylic acid In 5 ml. of a phosphate buffer solution of pH 6.4 are dissolved 0.459 g. of 7-(4-thiocyano-3-oxobutyrylamido)-3-(5-methyl-1,3,4-oxadiazol-2-yl)thiomethyl-3-cephem-4-carboxylic acid and 0.084 g. of sodium hydrogen carbonate and the solution is allowed to stand at room temperature overnight. This mixed solution is adjusted to pH 3 with 5% aqueous phosphoric acid solution and extracted with ethyl acetate (3×20 ml.). The ethyl acetate extract is washed with water, dehydrated and concentrated under reduced pressure. The concentrate thus obtained is allowed to stand and the resulting crystals are recovered by filtration. The procedure gives the above-identified product which is in good agreement with the product of Example 6 in IR and NMR spectra. Yield 0.283 g.

EXAMPLE 8

Production of 7-[2-(2-oxo-4-thiazolin-4-yl)acetamido]-3-(5-methyl-1,3,4-thiadiazol-2-yl)thiomethyl-3-cephem-4-carboxylic acid In 20 ml. of a phosphate buffer of pH 6.4 are dissolved 0.417 g. of 7-(4-thiocyano-3-oxobutyrylamido)-3-acetoxymethyl-3-cephem-4-carboxylic acid and 0.084 g. of sodium hydrogen carbonate and the solution is allowed to stand overnight.

In this mixed solution are dissolved 0.145 g. of 5-methyl-1,3,4-thiadiazole-2-thiol and 0.084 g. of sodium hydrogen carbonate, and the solution is stirred under heating at 60° C. for 6.5 hours. After cooling, the reaction mixture is rendered acid with 50% aqueous phosphoric acid solution, saturated with sodium chloride and extracted with a 2:1 mixture of ethyl acetate and tetrahydrofuran (3×20 ml.). The extract is washed with a saturated aqueous solution of sodium chloride, dehydrated and concentrated. The concentrate is allowed to stand and the resulting crystals are recovered by filtration. The described procedure gives 0.232 g. (yield 49%) of the above-indicated compound.

IR(cm$^{-1}$, KBr): 1786, 1655, 1535.

NMR($\delta$ in d$_6$-DMSO): 2.63(s, thiadiazole 5-CH$_3$), 3.30(s, CH$_2$CO), 3.53 & 3.77(ABq, J18.0 Hz, 2-CH$_2$), 4.18 & 4.49(ABq, J14.0Hz, 3-CH$_2$), 5.04(d, J5.0 Hz, 6-H), 5.65(dd, J5.0 & 8.0 Hz, 7-H), 5.98(s, thiazoline 5-H), 8.94(d, J8.0 Hz, CONH).

EXAMPLE 9

Production of 7-[2-(2-oxo-4-thiazolin-4-yl)acetamido]-3-(5-methyl-1,3,4-thiadiazol-2-yl)thiomethyl-3-cephem-4-carboxylic acid In 5 ml. of a phosphate buffer of pH 6.4 are dissolved 0.485 g. of 7-(4-thiocyano-3-oxobutyrylamido)-3-(5-methyl-1,3,4-thiadiazol-2-yl)thiomethyl-3-cephem-4-carboxylic acid and 0.084 g. of sodium hydrogen carbonate and the solution is allowed to stand at room temperature overnight. This mixed solution is adjusted to pH 3 with a 50% aqueous solution of phosphoric acid and extracted with ethyl acetate (3×20 ml.). The ethyl acetate extract is washed with water, dehydrated and concentrated under reduced pressure. The concentrate is allowed to stand and the resultant crystals are recovered by filtration. The above procedure gives the above-indicated compound which is in good agreement with the product according to Example 8 in IR and NMR spectra.

EXAMPLE 10

Production of sodium 7-[2-(2-aminothiazol-4-yl)acetamido]-3-acetoxymethyl-3-cephem-4-carboxylate In a mixture of 53 ml. of water and 26.4 ml. of tetrahydrofuran are dissolved 0.442 g. of thiourea and 0.889 g. of sodium hydrogen carbonate. Then, 2.3 g. of 7-(4-bromo-3-oxobutyrylamido)-3-acetoxymethyl-3-cephem-4-carboxylic acid is gradually added and dissolved. The mixture is stirred at room temperature for 30 minutes, after which time it is concentrated under reduced pressure to remove the tetrahydrofuran and further to a final volume of 20 ml. The residue is chromatographed on a column of polystyrene resin (Amberlite XAD-2) and developed with water. The fractions containing the desired product (with good absorption of ultraviolet light at 254 mμ) are pooled and freeze-dried. The procedure gives the above-indicated compound.

Yield 1.305 g. (52.6%).

IR(cm$^{-1}$, KBr): 1767.

UVλ max(ε in water): 256 nm(1.35×10$^4$).

NMR(δ in D$_2$O): 2.15 (s, CH$_3$CO), 3.39 & 3.69(ABq, J18 Hz, 2-CH$_2$), 3.62(s, CH$_2$CO), 4.75 & 4.94(ABq, J13 Hz, 3-CH$_2$), 5.15(d, J5 Hz, 6-H), 5.71(d, J5 Hz, 7-H), 6.52(s, thiazole 5-H).

Elemental analysis: Calcd. for C$_{15}$H$_{15}$N$_4$O$_6$S$_2$Na.2-H$_2$O: C, 38.29; H, 4.07; N, 11.91. Found: C, 38.41; H, 3.90; N, 11.72.

| Strain of microoganism | Antibacterial spectra (mcg/ml., agar dilution method) | | |
|---|---|---|---|
| | Product of this example | Cephaloridine | Cephazolin |
| S. aureus 209P | <0.78 | 0.05 | 0.1 |
| S. aureus 1840 | 1.56 | 0.39 | 1.56 |
| E. coli NIHJ JC-2 | 1.56 | 6.25 | 1.56 |
| K. pneumoniae DT | <0.78 | 3.125 | 1.56 |
| P. vulgaris Eb-57 | <0.78 | >100 | 50 |

EXAMPLE 11

Production of 7-[2-(2-aminothiazol-4-yl)acetamido]-3-acetoxymethyl-3-cephem-4-carboxylic acid In a mixture of 80 ml. of water and 40 ml. of tetrahydrofuran are dissolved 0.602 g. of thiourea and 0.664 g. of sodium hydrogen carbonate. Then, 3.085 g. of 7-(4-chloro-3-oxobutyrylamido)-3-acetoxymethyl-3-cephem-4-carboxylic acid is gradually added and dissolved. The mixture is stirred at room temperature for 1 hour, after which time the tetrahydrofuran is distilled off under reduced pressure. The residue is allowed to stand at room temperature and the resulting crystals are recovered by filtration. The filtrate is further concentrated and allowed to stand, whereupon an additional crop of crystals is obtained. These crystals are recovered and combined with those previously harvested. The described procedure gives 2.703 g. (83%) of the above-indicated compound.

IR(cm$^{-1}$, KBr): 1776.

UVλ max(ε in water): 256 nm(1.35×10$^4$).

NMR(δ in d$_6$-DMSO): 2.01(s, CH$_3$CO), 3.38(s, CH$_2$CO), 3.40 & 3.63 (ABq, J18 Hz, 2-CH$_2$), 4.68 & 4.98 (ABq, J13 Hz, 3-CH$_2$), 5.06(d, J5 Hz, 6-H), 5.68(dd, J5 & 8 Hz, 7-H), 6.23(s, thiazole 5-H), 6.90(broad s, NH$_2$), 8.82(d, J8 Hz, CONH), 9.20(broad s, COOH).

EXAMPLE 12

Production of sodium 7-[2-(2-methylaminothiazol-4-yl)acetamido]-3-acetoxymethyl-3-cephem-4-carboxylate In 10 ml. of water and 6 ml. of tetrahydrofuran are dissolved 0.099 g. of N-methylthiourea and 0.168 g. of sodium hydrogen carbonate. Then, 0.435 g. of 7-(4-bromo-3-oxobutyrylamido)-3-acetoxymethyl-3-cephem-4-carboxylic acid is gradually added and dissolved. The mixture is stirred at room temperature for 30 minutes, after which time the tetrahydrofuran is distilled off under reduced pressure. The residue is chromatographed on a column of polystyrene resin (Amberlite XAD-2) and developed with water. The fractions containing the desired product are pooled and freeze-dried. The procedure gives the above-indicated compound. Yield 0.16 g.

IR(cm$^{-1}$, KBr): 1763.

UVλ max(ε in water): 260 nm(1.48×10$^4$).

NMR(δ in D$_2$O): 2.15(s, CH$_3$CO), 2.92(s, CH$_3$N), 3.38 & 3.62(ABq, J18 Hz, 2-CH$_2$), 3.62(s, CH$_2$CO), 4.75 & 4.95(ABq, J13 Hz, 3-CH$_2$), 5.15(d, J5 Hz, 6-H), 5.71(d, J5 Hz, 6-H), 6.48(s, thiazole 5-H).

Elemental analysis: Calcd. for C$_{16}$H$_{17}$N$_4$O$_6$S$_2$Na.2.5-H$_2$O: C, 38.94; H, 4.49; N, 11.35. Found: C, 39.14; H, 4.27; N, 11.03.

EXAMPLE 13

Production of sodium 7-[2-(2-aminothiazol-4-yl)acetamido]-3-(1,3,4-thiadiazol-2-yl)thiomethyl-3-cephem-4-carboxylate In 20 ml. of a phosphate buffer of pH 6.4 are dissolved 0.47 g. of sodium 7-[2-(2-aminothiazol-4-yl)acetamido]-3-acetoxymethyl-3-cephem-4-carboxylate and 0.14 g. of 1,3,4-thiadiazole-2-thiol and the solution is stirred under heating at 55°–60° C. for 15 hours. After cooling, 0.084 g. of sodium hydrogen carbonate is added to the reaction mixture. The mixture is then chromatographed on a column of polystyrene resin (Amberlite XAD-2) and developed with water. The fractions containing the desired product are pooled and freeze-dried. The described procedures gives the above-indicated compound.

Yield 0.096 g.

IR(cm$^{-1}$, KBr): 1763.

UVλ max(ε in water): 262 nm(1.57×10$^4$).

NMR(δ in D$_2$O): 3.41 & 3.77(ABq, J18 Hz, 2-CH$_2$), 3.60(s, CH$_2$CO), 4.09 & 4.54(ABq, J13 Hz, 3-CH$_2$), 5.08(d, J5 Hz, 6-H), 5.65(d, J5 Hz, 7-H), 6.48(s, thiazole 5-H), 9.42(s, thiadiazol 5-H).

Elemental analysis: Calcd. for C$_{15}$H$_{13}$N$_6$O$_4$S$_4$Na.3.5-H$_2$O: C, 32.43; H, 3.63; N, 15.13. Found: C, 32.32; H, 3.05; N, 14.36.

| Strain of microoganism | Antibacterial spectra (mcg/ml., agar dilution method) | | |
|---|---|---|---|
| | Product of this example | Cephaloridine | Cephazolin |
| S. aureus 209P | <0.78 | 0.05 | 0.1 |
| S. aureus 1840 | <0.78 | 0.39 | 1.56 |
| E. coli 0-111 | <0.78 | 3.125 | 1.56 |
| K. pneumoniae DT | <0.78 | 3.125 | 1.56 |
| P. vulgaris Eb-58 | <0.78 | 12.5 | 6.25 |

EXAMPLE 14

Production of sodium 7-[2-(2-aminothiazol-4-yl)acetamido]-3-(1,3,4-thiadiazol-2-yl)thiomethyl-3-cephem-4-carboxylate In a mixture of 10 ml. of water and 10 ml. of tetrahydrofuran are dissolved 0.076 g. of thiourea and 0.084 g. of sodium hydrogen carbonate. Then, 0.449 g. of 7-(4-chloro-3-oxobutyrylamido)-3-(1,3,4-thiadiazol-2-yl)thiomethyl-3-cephem-4-carboxylic acid is added and dissolved. This reaction mixture is allowed to stand at room temperature overnight, after which time it is concentrated under reduced pressure to remove the tetrahydrofuran. To the residue is added 0.16 g. of sodium hydrogen carbonate and the mixture is chromatographed on a column of polystyrene resin (Amberlite XAD-2) using water as the developer solvent. The fractions containing the desired product are pooled and freeze-dried. The procedure gives the above-indicated compound which is in good agreement with the product of Example 13 in IR and NMR spectra. Yield 0.122 g.

EXAMPLE 15

Production of sodium 7-[2-(2-acetamidothiazol-4-yl)acetamido]-3-acetoxymethyl-3-cephem-4-carboxylate In a mixture of 10 ml. of water and 10 ml. of tetrahydrofuran are dissolved 0.13 g. of N-acetylthiourea and 0.168 g. of sodium hydrogen carbonate. Then, 0.435 g. of 7-(4-bromo-3-oxobutyrylamido)-3-cephem-4-carboxylic acid is gradually added and dissolved. The mixed solution is stirred at room temperature for 6 hours, after which time it is concentrated under reduced pressure to remove the tetrahydrofuran. The residue is chromatographed on a column of polystyrene resin (Amberlite XAD-2) and developed with water. The fractions containing the desired product are pooled and freeze-dried. The procedure gives the above-indicated compound. Yield 0.193 g.

IR(cm$^1$, KBr): 1764.

UVλ max (ε in water): 266 nm(1.60×10$^4$).

NMR(δ in D$_2$O): 2.09 (s, CH$_3$CON), 2.22(s, CH$_3$COO), 3.31 & 3.62(ABq, J18 Hz, 2-CH$_2$), 3.70(s, CH$_2$CO), 5.09(d, J5 Hz, 6-H), 5.66(d, J5 Hz, 7-H), 6.93(s, thiazole 5-H).

Elemental analysis: Calcd. for C$_{17}$H$_{17}$N$_4$O$_7$S$_2$Na.2.5-H$_2$O: C, 39.15; H, 4.25; N, 10.74. Found: C, 39.19; H, 4.01; N, 10.34.

EXAMPLE 16

Production of sodium 7-[2-(2-aminothiazol-4-yl)acetamido]-3-(1-methyltetrazol-5-yl)thiomethyl-3-cephem-4-carboxylate In a phosphate buffer of pH 6.4 are dissolved 0.47 g. of sodium 7-[2-(2-aminothiazol-4-yl)acetamido]-3-acetoxymethyl-3-cephem-4-carboxylate, 0.138 g. of 1-methyltetrazole-5-thiol and 0.084 g. of sodium hydrogen carbonate and the mixed solution is stirred under heating at 50°–55° C. for 16 hours. After cooling, this reaction mixture is chromatographed on a column of polystyrene resin (Amberlite XAD-2) and developed with water. The fractions containing the desired product are pooled and freeze-dried. The procedure gives the above-indicated compound. Yield 0.173 g.

IR(cm$^{-1}$, KBr): 1763.

UVλ max(ε in water): 260 nm(1.48×10$^4$).

NMR(δ in D$_2$O): 3.48 & 3.81(ABq, J17 Hz, 2-CH$_2$), 3.63(s, CH$_2$CO), 4.06(s, tetrazolyl 1-CH$_3$), 4.09 & 4.37(d, J14 Hz, 3-CH$_2$), 5.13(d, J5 Hz, 6-H), 5.68(d, J5 Hz, 7-H), 6.52(s, thiazole 5-H).

Elemental analysis: Calcd. for C$_{16}$H$_{15}$N$_8$O$_4$S$_3$.2.5-H$_2$O: C, 33.64; H, 3.76; N, 20.92. Found: C, 33.80; H, 3.33; N, 19.86.

| Strain of microoganism | Antibacterial spectra (mcg/ml., agar dilution method) | | |
|---|---|---|---|
| | Product of this example | Cephaloridine | Cephazolin |
| S. aureus 209P | 0.39 | 0.05 | 0.1 |
| S. aureus 1840 | 0.78 | 0.39 | 1.56 |
| E. coli NIHJ JC-2 | 0.39 | 6.25 | 1.56 |
| E. coli 0-111 | 0.2 | 3.125 | 1.56 |
| K. pneumoniae DT | <0.1 | 3.125 | 1.56 |
| P. vulgaris Eb 58 | 0.39 | 12.5 | 6.25 |
| P. morganii Eb 53 | 3.125 | >100 | 100 |

EXAMPLE 17

Production of sodium 7-[2-(2-aminothiazol-4-yl)acetamido]-3-(1-methyltetrazol-5-yl)thiomethyl-3-cephem-4-carboxylate In a mixture of 10 ml. of water and 10 ml. of tetrahydrofuran are dissolved 0.076 g. of thiourea and 0.084 g. of sodium hydrogen carbonate. Then, 0.447 g. of powdery 7-(4-chloro-3-oxobutyrylamido)-3-(1-methyltetrazol-5-yl)thiomethyl-3-cephem-4-carboxylic acid is added and dissolved. The reaction mixture is allowed to stand at room temperature overnight, after which it is concentrated under reduced pressure to remove the tetrahydrofuran. To the residue is added 0.16 g. of sodium hydrogen carbonate and the resultant mixture is chromatographed on a column of polystyrene resin (Amberlite XAD-2) and developed with water. The fractions containing the desired product are pooled and freeze-dried. The procedure gives the above-indicated compound which is in good agreement with the product of Example 16 in IR and NMR spectra. Yield 0.182 g.

EXAMPLE 18

Production of sodium 7-[2-(2-aminothiazol-4-yl)acetamido]-3-(5-methyl-1,3,4-thiadiazol-2-yl)thiomethyl-3-cephem-4-carboxylate In 20 ml. of a phosphate buffer of pH 6.4 are dissolved 0.47 g. of sodium 7-[2-(2-aminothiazol-4-yl)acetamido]-3-acetoxymethyl-3-cephem-4-carboxylate, 0.157 g. of 5-methyl-1,3,4-thiadiazole-2-thiol and 0.084 g. of sodium hydrogen carbonate and the mixed solution is stirred under heating at about 55° C. for 15 hours. After cooling, the reaction mixture is chromatographed on a column of polystyrene resin (Amberlite XAD-2) and developed with water. The fractions containing the desired product are pooled and freeze-dried. The described procedure gives the above-indicated compound. Yield 0.118 g.

IR($cm^{-1}$, KBr): 1763.

NMR($\delta$ in $D_2O$): 2.76(s, thiadiazole 5-$CH_3$), 3.42 & 3.79 (ABq, J18 Hz, 2-$CH_2$), 3.62(s, $CH_2CO$), 4.02 & 4.51(ABq, J14 Hz, 3-$CH_2$), 5.11 (d, J5 Hz, 6-H), 5.68(d, J5 Hz, 7-H), 6.50(s, thiazole 5-H).

Elemental analysis: Calcd. for $C_{16}H_{15}N_6O_4S_4Na.2.5-H_2O$: C, 34.84; H, 3.65; N, 15.23. Found: C, 34.87; H, 3.47; N, 14.82.

EXAMPLE 19

Production of sodium 7-[2-(2-aminothiazol-4-yl)acetamido]-3-(5-methyl-1,3,4-thiadiazol-2-yl)thiomethyl-3-cephem-4-carboxylate In a mixture of 10 ml. of water and 10 ml. of tetrahydrofuran are dissolved 0.076 g. of thiourea and 0.084 g. of sodium hydrogen carbonate. Then, 0.463 g. of 7-(4-chloro-3-oxobutyrylamido)-3-(5-methyl-1,3,4-thiadiazol-2-yl)thiomethyl-3-cephem-4-carboxylic acid is added and dissolved. The mixture is allowed to stand at room temperature overnight, after which it is concentrated under reduced pressure to remove the tetrahydrofuran. To the residue is added 0.16 g. of sodium hydrogen carbonate and the mixture is chromatographed on a column of polystyrene resin (Amberlite XAD-2) and developed with water. The fractions containing the desired product are pooled and freeze-dried. The procedure gives the above-indicated compound which is in good agreement with the product of Example 18 in IR and NMR spectra.

EXAMPLE 20

Production of sodium 7-[2-(N,N'-ethylene-2-imino-4-thiazolin-4-yl)acetamido]-3-acetoxymethyl-3-cephem-4-carboxylate In 10 ml. of water are dissolved 0.112 g. of N,N'-ethylene-thiourea and 0.168 g. of sodium hydrogen carbonate and, then, 0.39 g. of 7-(4-bromo-3-oxobutyrylamido)-3-acetoxymethyl-3-cephem-carboxylic acid is gradually added to the above solution. The mixture is allowed to stand at room temperature for 23 hours, after which time it is chromatographed on a column of polystyrene resin (Amberlite XAD-2) and developed with water. The fractions with good absorption of ultraviolet light (at 254 m$\mu$) are collected and freeze-dried. The procedure gives mixed crystals (1:3) of the above-indicated compound and its precyclization precursor compound, i.e. sodium 7-[4-(N,N'-ethyleneamidino)thio-3-oxobutyrylamido]-3-acetoxymethyl-3-cephem-4-carboxylate. Yield 0.084 g.

The following data are the values found for the above-mentioned mixed crystals.

IR($cm^{-1}$, KBr): 1768.

UV$\lambda$ max($\epsilon$ in water): 268 nm(1.23×$10^4$).

NMR($\delta$ in $D_2O$): 6.70(s, thiazoline 5-H).

Elemental analysis: Calcd. for $C_{17}H_{19}N_4O_7S_2Na.H_2O$: C, 41.13; H, 4.26; N, 11.29. Found: C, 40.98; H, 4.27; N, 11.13.

EXAMPLE 21

Production of sodium 7-[2-(2-thioxo-4-thiazolin-4-yl)-acetamido]-3-acetoxymethyl-3-cephem-4-carboxylate In a mixture of 10 ml. of water and 10 ml. of tetrahydrofuran are dissolved 0.22 g. of ammonium dithiocarbamate and 0.084 g. of sodium hydrogen carbonate. Then, 0.435 g. of 7-(4-bromo-3-oxobutyrylamido)-3-acetoxymethyl-3-cephem-4-carboxylic acid is added and dissolved. The mixture is stirred at room temperature for 45 minutes, after which time the tetrahydrofuran is distilled off under reduced pressure. The residue is rendered acid with 50% phosphoric acid and, then, extracted with ethyl acetate. The ethyl acetate extract is further extracted with 1% aqueous sodium hydrogen carbonate (2×15 ml.) and the water layers are pooled and chromatographed on a column of polystyrene resin (Amberlite XAD-2) using water as the developer solvent. The fractions absorbing ultraviolet light are collected and freeze-dried. The procedure gives mixed crystals (1:2) of the above-indicated compound and its precyclization precursor compound, i.e. sodium 7-(4-thiocarbamoylthio-3-oxobutyrylamido)-3-acetoxymethyl-3-cephem-4-carboxylate. Yield 0.21 g.

The following data are the values found for the above-mentioned mixed crystals.

IR($cm^{-1}$, KBr): 1762.

UV$\lambda$ max($\epsilon$ in water): 246 nm, 273 nm(1.84×$10^4$), 312 nm(4.12×$10^3$).

NMR($\delta$ in $D_2O$): the signals assignable to sodium 7-[2-(2-thioxo-4-thiazolin-4-yl)acetamido]-3-acetoxymethyl-3-cephem-4-carboxylate: 2.18(s, $C_3CO$), 3.43 & 3.74 (ABq, J18 Hz, 2-$CH_2$), 3.92(s, $COCH_2$), 4.78 & 4.98(ABq, J13 Hz, 3-$CH_2$), 5.21(d, J5 Hz, 6-H), 5.72(d, J5 Hz, 7-H), 6.93 (s, thiazoline 5-H); the signals assignable to sodium 7-(4-thiocarbamoylthio-3-oxobutyrylamido)-3-acetoxymethyl-3-cephem-4-carboxylate: 2.18(s, $CH_3CO$), 3.12(s, $SCH_2CO$), 3.49 & 3.79(ABq, J18 Hz, 2-$CH_2$), 4.78 & 4.98 (ABq, J13 Hz, 3-$CH_2$), 5.19 (d, J5 Hz, 6-H), 5.74(d, J5 Hz, 7-H).

Elemental analysis: Calcd. for $C_{15}H_{14}N_3O_6S_3Na.2.5-H_2O$: C, 36.29; H, 3.86; N, 8.46. Found: C, 36.08; H, 3.67; N, 8.25.

| | Antibacterial spectra (mcg/ml., agar dilution method) | | |
|---|---|---|---|
| Strain of microorganism | Product of this example | Cephaloridine | Cephazolin |
| S. aureus 209P | <0.78 | 0.05 | 0.1 |
| S. aureus 1840 | 1.56 | 0.39 | 1.56 |

EXAMPLE 22

Production of sodium 7-[2-(2-methylimino-3-methyl-4-thiazolin-4-yl)acetamido]-3-acetoxymethyl-3-cephem-4-carboxylate In a mixture of 10 ml. of water and 10 ml. of tetrahydrofuran are dissolved 0.115 g. of N,N'-dimethylthiourea and 0.168 g. of sodium hydrogen carbonate. Then, 0.435 g. of 7-(4-bromo-3-oxobutyrylamido)-3-acetoxymethyl-3-cephem-4-carboxylic acid is gradually added and dissolved. The mixture is allowed to stand at room temperature for 50 minutes, after which time it is concentrated under reduced pressure to remove the tetrahydrofuran. The residue is chromatographed on a column of polystyrene resin (Amberlite XAD-2) and developed in water. The fractions with good absorption of ultraviolet radiation (254 m$\mu$) are collected and freeze-dried. The procedure gives mixed crystals (1:2) of the above-indicated compound and its precyclization (uncyclized) precursor compound, i.e. sodium 7-(4-N,N'-dimethylamidinothio-3-oxobutyrylamido)-3-acetoxymethyl-3-cephem-4-carboxylate. Yield 0.15 g.

The following data are the values found for the above-mentioned mixed crystals.

IR(cm$^{-1}$, KBr): 1773.

NMR($\delta$ in D$_2$O): the signals assignable to sodium 7-[2-(2-methyl-imino-3-methyl-4-thiazolin-4-yl)acetamido]-3-acetoxymethyl-3-cephem-4-carboxylate; 2.12(s, CH$_3$CO), 3.08(s, thiazoline 3-CH$_3$), 3.11(s, CH$_3$—N=), 3.39 & 3.70(ABq, J18 Hz, 2-CH$_2$), 3.91(s, CH$_2$CO), 4.73 & 4.92 (ABq, J13 Hz, 3-CH$_2$), 5.14(d, J5 Hz, 6-H), 5.63(d, J5 Hz, 7-H), 6.86(s, thiazoline 5-H); the signals assignable to sodium 7-(4-N,N'-dimethylamidinothio-3-oxobutyrylamido)-3-acetoxymethyl-3-cephem-4-carboxylate: 2.12 (s, CH$_3$CO), 3.08(s, CH$_3$NH), 3.11(s, CH$_3$—N=), 3.39 & 3.70(ABq, J18 Hz, 2-CH$_2$), 3.51(s, SCH$_2$CO), 4.73 & 4.92 (ABq, J13 Hz, 3-CH$_2$), 5.16(d, J5 Hz, 6-H), 5.67(d, J5 Hz, 7-H).

Elemental analysis: Calcd. for C$_{17}$H$_{19}$N$_4$O$_6$S$_2$Na.1.5-H$_2$O: C, 41.71; H, 4.53; N, 11.45. Found: C, 42.08; H, 4.98; N, 11.47.

EXAMPLE 23

The compounds listed in Tables 1 to 14 are prepared by one or more of the following Methods 1 to 10.

Method 1

(1) In 40 ml. of water are dissolved 10.7 g. (30 m mol) of 7-acetoacetamido-3-acetoxymethyl-3-cephem-4-carboxylic acid, 30 m mol of a nitrogen-containing heterocyclic thiol and 5.04 g. (60 m mol) of sodium hydrogen carbonate and the solution is adjusted at pH 7.0 with a 10% aqueous solution of sodium hydroxide, followed by stirring for 4 hours at 60°–65° C. After cooling, 2.31 g. (33 m mol) of hydroxylamine hydrochloride is added to the reaction mixture and the mixture is adjusted to pH 3.6 by adding N-hydrochloric acid, followed by standing at room temperature for overnight. The precipitated crystals of a 7-amino-3-(nitrogen-containing heterocyclic) thiomethyl-3-cephem-4-carboxylic acid are collected by filtration, washed with acetone and dried.

(2) A solution of 1.03 g. (13 m mol) of diketene in 5 ml. of methylene chloride is previously chilled to −30° C. and a solution of 1.05 g (15 m mol) of chlorine in 10 ml. of carbon tetrachloride or a solution of 2.24 g. (14 m mol) of bromine in 5 ml. of methylene chloride is added dropwise thereto. Meanwhile, 10 m mol of a 7-amino-3-(nitrogen-containing heterocyclic)thiomethyl-3-cephem-4-carboxylic acid and 2.02 g. (20 m mol) of triethylamine are dissolved in 20 ml. of methylene chloride and the solution is chilled to −20° C. To this solution is dropped rapidly the above-prepared reaction mixture. The temperature rises in most cases to the neighborhood of 0° C. caused by the exothermic reaction. After the exothermic reaction is subsided, the temperature is gradually increased to room temperature. After stirring for 15 minutes, the reaction solution is added to a mixture of 150 ml. of ethyl acetate and 100 ml. of a 10% aqueous solution of phosphoric acid under vigorous stirring. The organic layer is separated, washed with water and dried, followed by the evaporation of the solvent. To the residue is added ether and the mixture is allowed to stand. The resultant precipitate of a 7-(4-chloro or bromo-3-oxobutyrylamido)-3-(nitrogen-containing heterocyclic)thiomethyl-3-cephem-4-carboxylic acid is recovered by filtration as powder.

(3) To a mixed solution of 0.304 g. (4 m mol) of thiourea, 2 ml. of tetrahydrofuran and 1 ml. of water, is added dropwise a solution of 2 m mol of 7-(4-chloro or bromo)-3-oxobutyrylamido)-3-(nitrogen-containing heterocyclic)thiomethyl-3-cephem-4-carboxylic acid (2 m mol) in 3 ml. of tetrahydrofuran and a solution of 0.18 g. (2.2 m mol) of sodium hydrogen carbonate in 2 ml. of water at the same time, followed by stirring for 3 hours. The reaction mixture is subjected to the distillation of the organic solvent and the residue is dissolved in 4 ml. of 0.5 N-aqueous solution of sodium hydroxide. The solution is chromatographed on a column of polystyrene resin (Amberlite XAD-2) and subjected to a development with a gradient elution starting from water to 40% methanol. The fractions containing the desired product are pooled and freeze-dried to give a sodium 7-[2-(2-aminothiazol-4-yl)acetamido]-3-(nitrogen-containing heterocyclic)thiomethyl-3-cephem-4-carboxylate.

Method 2

(1) A solution of 60 g. (0.2 mol) of 7-formamido-3-acetoxymethyl-3-cephem-4-carboxylic acid, 0.2 mol of a nitrogen-containing heterocyclic thiol and 33.6 g. (0.4 mol) of sodium hydrogen carbonate dissolved in 200 ml. of water is adjusted to pH 7.0 by adding a 10% aqueous solution of sodium hydroxide and stirred for 4–5 hours at 60°–65° C., followed by addition of 500 ml. of methanol. The mixture is cooled down with ice and 80 g. of concentrated sulfuric acid is added thereto under stirring and keeping the temperature not exceeding 30° C., followed by standing in ice-room overnight. The reaction mixture is diluted with 1000 ml. of water and the mixed solution is shaken with ethyl acetate (2×400 ml.). The combined aqueous layer is subjected to the filtration under suction to remove undissolved materials and the filtrate is adjusted to pH 3.8 by adding concentrated aqueous ammonia, followed by standing at 0° C. for 3 hours. The precipitated crystals are collected by filtration and washed with cold water (100 ml.) and then acetone (300 ml.), followed by drying to give 7-amino-3-(nitrogen-containing heterocyclic) thiomethyl-3-cephem-4-carboxylic acid.

(2) The material obtained in above (1) is treated in the similar manner as (2) and (3) of Method 1 to obtain a sodium 7-[2-(2-aminothiazol-4-yl)acetamido]-3-(nitrogen-containing heterocyclic)thiomethyl-3-cephem-4-carboxylate.

Method 3

A solution of 0.824 g. (2 m mol) of 7-[2-(2-aminothiazol-4-yl)acetamido]-3-acetoxymethyl-3-cephem-4-carboxylic acid, 2.2 m mol of a nitrogen-containing heterocyclic thiol and 0.336 g. (4 m mol) of sodium hydrogen carbonate dissolved in 8 ml. of water (when homogenous solution is not attained, 4 ml. of tetrahydrofuran is added) is stirred for 6–8 hours under heating at 60°–65° C. After cooling, the reaction mixture is subjected to the distillation of tetrahydrofuran under suction and the residue is chromatographed on a column of polystyrene resin (Amberlite XAD-2), followed by development with a gradient elution starting from water to 40% methanol. The fractions containing the desired product are pooled and freeze-dried to give a sodium 7-[2-(2aminothiazol-4-yl)acetamido]-3-(nitrogen-containing heterocyclic)thiomethyl-3-cephem-4-carboxylate.

Method 4

In 40 ml. of a phosphate buffer of pH 6.4 are dissolved 0.824 g. (2 m mol) of 7-[2-(2-aminothiazol-4-yl)acetamido]-3-acetoxymethyl-3-cephem-4-carboxylic acid, 2.2 m mol of a nitrogen-containing heterocyclic thiol and 0.336 g. (4 m mol) of sodium hydrogen carbonate and the solution is stirred for 7–8 hours under heating at 60°–65° C. The reaction solution is concentrated to about 20 ml. under reduced pressure and the concentrate is chromatographed on a column of polystyrene resin (Amberlite XAD-2), followed by development with water, 5% ethanol and 10% ethanol in this order. The fractions containing the desired product are pooled and freeze-dried to give a sodium 7-[2-(2-aminothiazol-4-yl)acetamido]-3-(nitrogen-containing heterocyclic)-thiomethyl-3-cephem-4-carboxylate.

Method 5

A mixed solution of 0.824 g. (2 m mol) of 7-[2-(2-aminothiazol-4-yl)acetamido]-3-acetoxymethyl-3-cephem-4-carboxylic acid, 0.596 g. (2 m mol) of 2-(2-benzoyloxyethylthio)-1,3,4-thiadiazole-5-thiol, 0.336 g. (4 m mol) of sodium hydrogen carbonate, 5 ml. of tetrahydrofuran and 10 ml. of water is heated at 65° C. for 5 hours. The reaction solution is concentrated to dryness and the residue is dissolved in 4 ml. of acetonitrile. The solution is chromatographed on a column of silica-gel and developed with a 5% aqueous solution of acetonitrile and then a 15% aqueous solution of acetonitrile. The fractions containing the desired product are pooled and concentrated to precipitate crystals which are collected by filtration to obtain 0.43 g. of 7-[2-(2-aminothiazol-4-yl)acetamido]-3-[2-(2-benzoyloxyethylthio)-1,3,4-thiadiazol-5-yl]thiomethyl-3-cephem-4-carboxylic acid.

Method 6

(1) In 100 ml. of acetonitrile are dissolved 0.1 mol of a 7-(4-chloro or bromo-3-oxobutyrylamido)-3-(nitrogen-containing heterocyclic)thiomethyl-3-cephem-4-carboxylic acid and 14.5 g. (0.15 mol) of potassium thiocyanate and the solution is stirred for 16 hours at room temperature. The reaction solution is subjected to the distilation of the solvent under reduced pressure and to the residue is added 50 ml. of a saturated aqueous solution of sodium chloride. The mixture is adjusted to pH 3 with 50% phosphoric acid and extracted with ether (2×100 ml.). The combined extract is washed with a saturated aqueous solution of sodium chloride and dried, followed by concentration to dryness. The residue is triturated with ether and the mixture is allowed to stand. The resultant precipitate of a 7-(4-thiocyano-3-oxobutyrylamido)-3-(nitrogen-containing heterocyclic) thiomethyl-3-cephem-4-carboxylic acid is recovered by filtration as a powder.

(2) In 50 ml. of a phosphate buffer solution of pH 6.4 are dissolved 10 m mol of 7-(4-thiocyano-3-oxobutyrylamido)-3-(nitrogen-containing heterocyclic)thiomethyl-3-cephem-4-carboxylic acid and 0.84 g. (10 m mol) of sodium hydrogen carbonate and the solution is allowed to stand at room temperature for 2 days. The mixed solution is adjusted to pH 3.0 with 50% phosphoric acid and saturated with sodium chloride, followed by the extraction with ethyl acetate (3×100 ml.). The combined extract is washed with 10% aqueous solution of sodium chloride and dried. The dried solution is concentrated and to the concentrate is added ether, followed by standing. The precipitated crystals are collected by filtration under suction to obtain a 7-[2-(2-oxo-4-thiazolin-4-yl) acetamido]-3-(nitrogen-containing heterocyclic)thiomethyl-3-cephem-4-carboxylic acid.

Method 7

In a mixture of 8 ml. of water and 4 ml. of tetrahydrofuran are dissolved 0.974 g. (2 m mol) of 7-[2-(2-oxo-4-thiazolin-4-yl)acetamido]-3-acetoxymethyl-3-cephem-4-carboxylic acid, 1.1 m mol of a nitrogen-containing heterocyclic thiol and 0.336 g. (4 m mol) of sodium hydrogen carbonate and the resultant solution is stirred under heating at 60°–65° C. for 6–8 hours. After cooling, the reaction solution is adjusted pH 3.0 by adding phosphoric acid and extracted with ethyl acetate, followed by washing with water and drying. The dried extract is concentrated to dryness under reduced pressure and the residue is triturated with ether followed by standing. The precipitate is collected by filtration to give 7-[2-(2-oxo-4-thiazolin-4-yl)acetamido]-3-(nitrogen-containing heterocyclic)thiomethyl-3-cephem-4-carboxylic acid as powder.

Method 8

(1) In 4 ml. of tetrahydrofuran are dissolved 0.159 g. (1 m mol) of (2-oxo-4-thiazolin-4-yl)acetic acid, 0.115 g. (1 m mol) of N-hydroxysuccinimide and 0.206 g. of dicyclohexylcarbodiimide and the solution is stirred for one hour at room temperature. The reaction mixture is subjected to filtration under suction to remove the precipitate of N,N'-dicyclohexylurea.

The filtrate is added at a stroke to a solution of 1.2 m mol of a 7-amino-3-(nitrogen-containing heterocyclic) thiomethyl-3-cephem-4-carboxylic acid and 0.15 g. (1.5 m mol) of triethylamine dissolved in 15 ml. of dichloromethane and the mixture is stirred for 2 hours at room temperature. The solvent is distilled off under suction from the reaction mixture and to the residue is added water, followed by adjusting to pH 2.5 with concentrated phosphoric acid. The resultant solution is extracted with ethyl acetate (3×60 ml.) and the extract is washed with water and dried, followed by concentration under suction. The residue is triturated with ether, and the mixture is allowed to stand. The precipitates are collected by filtration to obtain a 7-[2-(2-oxo-4-thiazolin-4-yl)acetamido]-3-(nitrogen-containing heterocyclic)thiomethyl-3-cephem-4-carboxylic acid.

Method 9

(1) In 10 ml. of dimethylformamide are dissolved 0.4 g. (2 m mol) of 2-(2-aminothiazol-4-yl)acetic acid hydrochloride, 0.25 g. (2.2 m mol) of N-hydroxysuccinimide and 0.412 g. (2 m mol) of dicyclohexylcarbodiimide and the solution is allowed to stand at room temperature for 3 hours. The reaction mixture is subjected to filtration under suction to remove the precipitate of N,N'-dicyclohexylurea.

(2) The filtrate is added at a stroke to a solution of 2 m mol of 7-aminocephalosporanic acid or a 7-amino-3-(nitrogen-containing heterocyclic)thiomethyl-3-cephem-4-carboxylic acid and 0.404 g. (4 m mol) of triethylamine dissolved in 20 ml. of dichloromethane and the mixed solution is stirred for 24 hours at room temperature. The solvent is distilled off under reduced pressure and the residue is adjusted its pH to 7 by adding a 10% aqueous solution of sodium hydrogen carbonate. The resultant solution is chromatographed on column of polystyrene resin (Amberlite XAD-2) and developed with water and then with 5% ethanol. The fractions containing the desired product are pooled and freeze-dried to obtain the corresponding sodium 7-[2-(2-aminothiazol-4-yl)acetamido]-3-(acetoxymethyl or nitrogen-containing heterocyclic thiomethyl)-3-cephem-4-carboxylate.

Method 10

To 3 ml. of phosphorous oxychloride is added 0.35 g. of (2-thioxo-4-thiazolin-4-yl)acetic acid and the mixture is heated at 80°–90° C. for 15 minutes to give homogenous solution, followed by distillation of excess phosphorous oxychloride under reduced pressure. The residue is dissolved in 5 ml. of acetone and the solution is added dropwise to a mixed solution of 2 m mol of 7-aminocephalosporanic acid or a 7-amino-3-(nitrogen-containing heterocyclic)thiomethyl-3-cephem-4-carboxylic acid, 6 ml. of acetone and 10 ml. of water which is adjusted to pH 6.8 with a 10% aqueous solution of sodium hydrogen carbonate under ice-cooling and stirring, while the pH of the solution is maintained in the range from 6 to 7 by adding a 10% aqueous solution of sodium hydrogen carbonate. After stirring for further 2 hours, the mixture is subjected to the distillation under suction to remove acetone and the residue is chromatographed on a column of polystyrene resin (Amberlite XAD-2), followed by developing with water. The fractions containing desired product are pooled and freeze-dried to obtain the corresponding 7-[2-(2-thioxo-4-thiozolin-4-yl)acetamido]-3-acetoxymethyl or (nitrogen-containing heterocyclic)thiomethyl-3-cephem-4-carboxylic acid.

TABLE 1

[Structure: HN=C(S)-NH-C(=CH...)-CH$_2$CONH-[β-lactam]-CH$_2$S-[thiadiazole]-R$^5$, with COOM group]

| Compound No. | R$^5$ | M | UV$\lambda_{max}$ ($\epsilon$ in water) | IR (KBr) cm$^{-1}$ | NMR $\delta$ ppm | Method No. |
|---|---|---|---|---|---|---|
| 1 | —SH | Na | — | 1760 | (60MHz, in D$_2$O): 3.4–3.7(m,2xCH$_2$), 3.9–4.31(ABq, J14Hz,3-CH$_2$), 5.08(d,J5Hz,6-H), 5.64(d,J5Hz,7-H), 6.50(s,thiazole 5-H). | 3 |
| 2 | —SCH$_3$ | Na | — | 1760 | (60MHz, in D$_2$O): 2.70(s,CH$_3$), 3.45–3.70(m,2xCH$_2$) 3.95–4.34(ABq, J14Hz,3-CH$_2$), 5.10(d,J5Hz,6-H), 5.70(d,J5Hz,7-H), 6.55(s,thiazole 5-H). | 3 |
| 3 | —CH$_2$N$^{\oplus}$H(morpholino) | ⊖ | 262nm (1.53 × 10$^4$) | 1769 | (100MHz, in D$_2$O): 2.74(m,4H), 3.53 & 3.87(ABq,J18Hz, 2-CH$_2$), 3.70(s, CH$_2$CO), 3.88(m,4H), 4.15(s,=NCH$_2$), 4.20 & 4.59(Abq, J13Hz,3-CH$_2$), 5.20(d,J5Hz,6-H), 5.76(d,J5Hz,7-H), 6.58(s,thiazole 5-H). | 1 4 |
| 4 | —NH$_2$ | Na | 260nm (1.61 × 10$^4$) | 1760 | (100MHz, in D$_2$O): 3.44 & 3.88(ABq, J18Hz,2-CH$_2$), 3.70 (s,CH$_2$CO), 3.89 & | 1 2 4 |

TABLE 1-continued

Structure (shown at top of table):
HN=C(S)-NH-...-CH₂CONH- attached to β-lactam-thiazine core with -COOM and -CH₂S-[thiadiazole]-R⁵ substituent.

| Compound No. | R⁵ | M | UVλ_max (ε in water) | IR (KBr) cm⁻¹ | NMR δ ppm | Method No. |
|---|---|---|---|---|---|---|
| | | | | | 4.51(ABq,J13Hz, 3-CH₂), 5.19(d, J5Hz,6-H), 5.75 (d,J5Hz,7-H), 6.60 (s,thiazole 5-H). | |
| 5 | —NHCOOCH₃ | Na | 261nm (1.61 × 10⁴) | 1760 | (100MHz, in D₂O): 3.47 & 3.88(ABq, J18Hz,2-CH₂), 3.71 (s,CH₂CO), 3.89(s, OCH₃), 3.90 & 4.51 (ABq,J13Hz,3-CH₂), 5.19(d,J5Hz,6-H), 5.75(d,J5Hz,7-H), 6.59(s,thiazole 5-H). | 1 2 4 |
| 6 | —SCH₂CH₂OH | Na | 260nm (1.65 × 10⁴) | 1765 | (60MHz, in D₂O): 3.4–3.8(m,3xCH₂), 3.95(t,J6Hz,CH₂O), 4.00 & 4.40(ABq, J14Hz,3-CH₂), 5.05(d,J5Hz,6-H), 5.62(d,J5Hz,7-H), 6.52(s,thiazole 5-H). | 1 2 3 |
| 7 | —NHCOCH₂N(CH₃)₂ | Na | 261nm (1.62 × 10⁴) | 1760 | (60MHz, in D₂O): 2.95(s,2xCH₃), 3.40–4.10(m,4xCH₂), 5.02(d,J5Hz,6-H), 5.59(d,J5Hz,7-H), 6.42(s,thiazole 5-H). | 1 2 3 |
| 8 | —CH₂CON(CH₃)₂ | Na | 260nm (1.48 × 10⁴) | 1757 | (100MHz, in D₂O): 3.12 & 3.28(each s,N(CH₃)₂), 3.54 & 3.89(ABq,J18Hz, 2-CH₂), 3.72(s, CH₂CO), 4.20 & 4.61(ABq,J14Hz, 3-CH₂), 5.22(d, J5Hz,6-H), 5.78 (d,J5Hz,7-H), 6.61(s,thiazole 5-H). | 1 2 4 |
| 9 | —SCH₂CH₂N(CH₃)₂ | Na | 260nm (1.54 × 10⁴) | 1768 | (60MHz, in D₂O) 2.74(s,2xCH₃), 3.2–3.8(m,4xCH₂), 4.14 & 4.54(ABq, J14Hz,3-CH₂), 5.00(d,J5Hz,6-H), 5.56(d,J5Hz,7-H), 6.23(s, thiazole 5-H). | 1 2 3 |
| 10 | —SCH₂CH₂OCOC₆H₅ | H | in 1% NaHCO₃: 233nm (2.14 × 10⁴) 260nm (1.71 × 10⁴) | 1772 | (60MHz, in D₂O—d₆-DMSO): 3.3–3.8(m,3xCH₂), 4.12 & 4.52(ABq, J14Hz,3-CH₂), 4.58 (t,J6Hz,CH₂O), 5.02(d,J5Hz,6-H), 5.60(d,J5Hz,7-H), 6.28(s,thiazole 5-H), 7.4–7.9(m, 5H). | 5 |
| 11 | —SCH₂CH₂OCOCH₃ | Na | 260nm (1.68 × 10⁴) | 1763 | (60MHz, in D₂O): 2.00(s,CH₃CO), 3.2–3.7(m,6H), 4.0–4.4(m,4H), 5.00(d,J5Hz,6-H), | 3 |

TABLE 1-continued

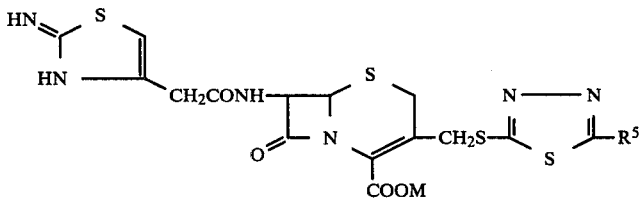

| Compound No. | $R^5$ | M | UV$\lambda_{max}$ ($\epsilon$ in water) | IR (KBr) cm$^{-1}$ | NMR $\delta$ ppm | Method No. |
|---|---|---|---|---|---|---|
| 12 | —SCH$_2$CH$_2$SO$_3$Na | Na | 261nm (1.70 × 10$^4$) | 1763 | 5.57(d,J5Hz,7-H), 6.46(s,thiazole 5-H). (60MHz, in D$_2$O): 3.0–3.8(m,8H), 4.00 & 4.27(ABq, J13Hz,3-CH$_2$), 5.03(d,J5Hz,6-H), 5.58(d,J5Hz,7-H), 6.48(s,thiazole 5-H). | 3 |
| 13 | —SCH$_2$COOC$_2$H$_5$ | Na | 261nm (1.75 × 10$^4$) | 1763 | (60MHz, in D$_2$O): 1.23(t,J7Hz,CH$_3$CH$_2$), 3.4–4.5 (m,10H), 5.04 (d,J5Hz,6-H), 5.64(d,J5Hz,7-H), 6.45(s,thiazole 5-H). | 1 2 3 |
| 14 | —SCH$_2$CON⌒O⌣ | Na | 260nm (1.73 × 10$^4$) | 1763 | (60MHz, in D$_2$O): 3.3–4.5(m,16H), 5.07(d,J5Hz,6-H), 5.63(d,J5Hz,7-H), 6.48(s,thiazole 5-H) | 1 2 3 |
| 15 | —SCH$_2$COONa | Na | 261nm (1.67 × 10$^4$) | 1763 | (60MHz, in D$_2$O): 3.36 & 3.76(ABq, J16Hz,2-CH$_2$),3.60 (s,CH$_2$CON), 3.96 & 4.40(Abq,J14Hz, 3-CH$_2$), 5.08(d, J5Hz,6-H), 5.63 (d,J5Hz,7-H), 6.48(s,thiazole 5-H). | 1 2 3 |
| 16 | —SCH$_2$CONH$_2$ | Na | 261nm (1.69 × 10$^4$) | 1768 | (60MHz, in D$_2$O): 3.49 & 3.69(ABq, J18Hz,2-CH$_2$), 3.59(s,CH$_2$CO), 4.04(s,SCH$_2$CO), 4.00 & 4.42(ABq, J14Hz,3-CH$_2$), 5.03(d,J5Hz,6-H), 5.60(d,J5Hz,7-H), 6.47(s,thiazole 5-H). | 1 2 4 |
| 17 | —NHCH$_2$CH$_2$OH | Na | 260nm (1.63 × 10$^4$) | 1765 | (60MHz, in D$_2$O): 3.3–3.95(m,8H), 4.32(ABq,3-CH$_2$), 4.97(d,J5Hz,6-H), 5.53(d,J5Hz,7-H), 6.40(s,thiazole 5-H). | 1 2 3 |
| 18 | —NCH$_2$CH$_2$N(CH$_3$)$_2$ | Na | 255nm (2.12 × 10$^4$) | 1760 | (60MHz, in D$_2$O): 2.95(s,6H), 3.55 (m,6H),3.95(ABq, 2-CH$_2$), 4.35(ABq, 3-CH$_2$), 5.02(d, J5Hz,6-H), 5.55 (d,J5Hz,7-H), 6.38 (s,thiazole 5-H) | 1 2 3 |
| 19 | —CH$_2$COONa | Na | 262nm (1.76 × 10$^4$) | 1761 | (100MHz, in D$_2$O): 3.56 & 3.92(ABq, J18Hz,2-CH$_2$), 3.76 (s,CH$_2$CO), 4.16(s, CH$_2$CO), 4.20 & 4.62 (ABq,J13Hz,3-CH$_2$), 5.24(d,J5Hz,6-H), | 1 2 4 |

TABLE 1-continued

| Compound No. | R[5] | M | UVλ$_{max}$ (ε in water) | IR (KBr) cm$^{-1}$ | NMR δ ppm | Method No. |
|---|---|---|---|---|---|---|
| | | | | | 5.79(d,J5Hz,7-H), 6.65(s,thiazole 5-H). | |
| 20 | —CH$_2$COOCH$_3$ | Na | 261nm (1.64 × 10$^4$) | 1757 | (100MHz, in D$_2$O): 3.52 & 3.87(ABq, J18Hz,2-CH$_2$), 3.70 (s,CH$_2$CO), 3.91(s, OCH$_3$), 4.18 & 4.58 (ABq,J13Hz,3-CH$_2$), 5.20(d,J5Hz,6-H), 5.75(d,J5Hz,7-H), 6.60(s,thiazole 5-H). | 1 2 4 |
| 21 | —CH$_2$CONH$_2$ | Na | 260nm (1.64 × 10$^4$) | 1762 | (100MHz, in D$_2$O): 3.51 & 3.86 (ABq, J18Hz,2-CH$_2$), 3.70 (s,CH$_2$CO), 4.18 & 4.57(ABq,3-CH$_2$), 5.19(d,J5Hz,6-H), 5.75(d,J5Hz,7-H), 6.58(s,thiazole 5-H). | 1 2 4 |
| 22 | —NHCH$_2$CH$_2$SO$_3$Na | Na | 260nm (1.67 × 10$^4$) | 1760 | (60MHz, in D$_2$O): 3.23(t,J6Hz,CH$_2$SO$_3$), 3.5–3.7(m,3xCH$_2$), 4.05 & 4.45(ABq, J13Hz,3-CH$_2$), 5.04 (d,J5Hz,6-H), 5.58 (d,J5Hz,7-H), 6.48 (s,thiazole 5-H). | 3 |
| 23 | —SCH$_2$COCH$_3$ | Na | 260nm (1.58 × 10$^4$) | 1765 | (60MHz, in D$_2$O): 2.40(s,CH$_3$), 3.4– 3.8(m,2xCH$_2$), 4.05 & 4.35(ABq,J14Hz, 3-CH$_2$), 4.30(s, CH$_2$CO), 5.08(d, J5Hz,6-H), 5.62(d, J5Hz,7-H), 6.42(s, thiazole 5-H). | 3 |
| 24 | —CH$_2$SCH$_3$ | Na | 262nm (1.63 × 10$^4$) | 1762 | (100MHz, in D$_2$O): 2.24(s,CH$_3$S), 3.53 & 3.85(ABq,J18Hz, 2-CH$_2$), 3.72(s,CH$_2$ CO), 4.21(s,CH$_2$S), 4.25 & 4.59(ABq, J14Hz,3-CH$_2$), 5.20 (d,J5Hz,6-H), 5.78 (d,J5Hz,7-H), 6.58 (s,thiazole 5-H). | 1 2 4 |
| 25 | —CH$_2$SO$_2$CH$_3$ | Na | 261nm (1.64 × 10$^4$) | 1765 | (100MHz, in D$_2$O): 3.32(s,CH$_3$SO$_2$), 3.53 & 3.84(Abq, J18Hz,2-CH$_2$), 3.70 (s,CH$_2$CO), 4.23 & 4.59(ABq,J14Hz, 3-CH$_2$), 5.19 & 5.74 (each d, J5Hz, 6- & 7-H), 6.58(s, thiazole H). | 1 2 4 |
| 26 | —CH$_2$CON⟨O⟩ | Na | 262nm (1.65 × 10$^4$) | 1770 | (100MHz, in D$_2$O): 3.4–4.4(m,12H), 5.21(d,J5Hz,6-H), 5.77(d,J5Hz,7-H), 6.60(s,thiazole 5-H). | 1 2 4 |
| 27 | —SCH$_2$CON(CH$_3$)$_2$ | Na | 260nm (1.70 × 10$^4$) | 1765 | (60MHz, in D$_2$O): 2.95 & 3.14(each s, 2xCH$_3$), 3.5– | 1 2 3 |

TABLE 1-continued

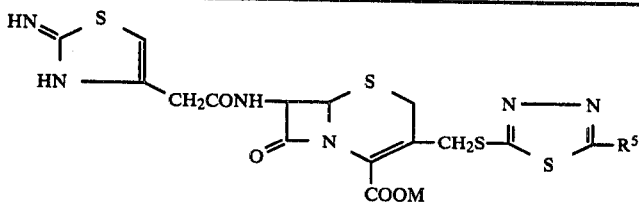

| Compound No. | R[5] | M | UVλ$_{max}$ (ε in water) | IR (KBr) cm$^{-1}$ | NMR δ ppm | Method No. |
|---|---|---|---|---|---|---|
| | | | | | 4.4(m,4×CH$_2$), 5.04 (d, J5Hz,6-H), 5.64 (d,J5Hz,7-H), 6.45 (s,thiazole 5-H). | |

TABLE 2

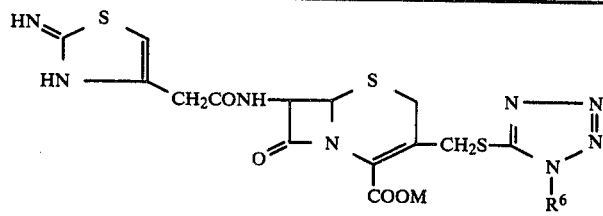

| Compound No. | R[6] | M | UVλ$_{max}$ (ε in water) | IR (KBr) cm$^{-1}$ | NMR δ ppm | Method No. |
|---|---|---|---|---|---|---|
| 28 | —CH$_2$CH$_2$N(CH$_3$)$_2$ | Na | 261nm (1.71 × 10$^4$) | 1765 | (60MHz, in D$_2$O): 2.79(s,2 × CH$_3$), 3.5–4.8(m,5 × CH$_2$), 5.09(d,J5Hz,6-H), 5.65(d,J5Hz,7-H), 6.48(s,thiazole 5-H). | 1 2 3 |
| 29 | —CH$_2$CONH$_2$ | Na | 259nm (1.48 × 10$^4$) | 1765 | (100MHz, in D$_2$O): 3.52 & 3.84(ABq, J18Hz,2-CH$_2$), 3.72(s,CH$_2$CO), 4.24 & 4.49(ABq, J13Hz,3-CH$_2$), 5.20 (d,J5Hz,6-H), 5.42 (s,NCH$_2$CO), 5.76 (d,J5Hz,7-H), 6.62 (s,thiazole 5-H). | 1 2 4 |

TABLE 3

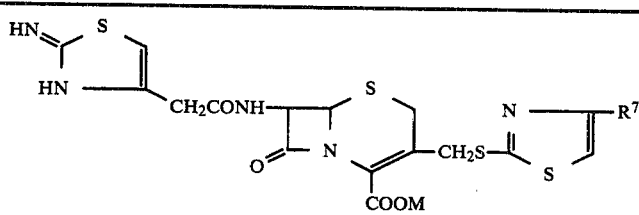

| Compound No. | R[7] | M | UVλ$_{max}$ (ε in water) | IR (KBr) cm$^{-1}$ | NMR δ ppm | Method No. |
|---|---|---|---|---|---|---|
| 30 | —CH$_2$COONa | Na | 259nm (1.66 × 10$^4$) | 1763 | (100MHz, in D$_2$O): 3.44 & 3.83(ABq, J18Hz,2-CH$_2$), 3.69 (s,CH$_2$CO), 3.76(s, CH$_2$CO), 3.99 & 4.57(ABq,J14Hz, 3-CH$_2$), 5.15(d, J5Hz,6-H), 5.72 (d,J5Hz,7-H), 6.58(s,7 positioned thiazole | 1 4 |

TABLE 3-continued

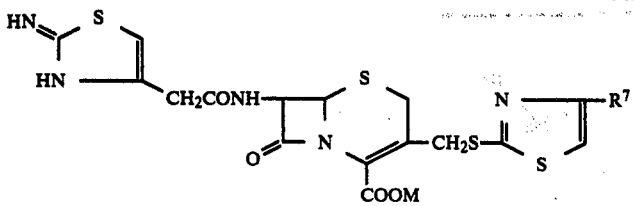

| Compound No. | R[7] | M | UVλ$_{max}$ (ε in water) | IR (KBr) cm$^{-1}$ | NMR δ ppm | Method No. |
|---|---|---|---|---|---|---|
| | | | | | 5-H), 7.35(s,3 positioned thiazole 5-H). | |

TABLE 4

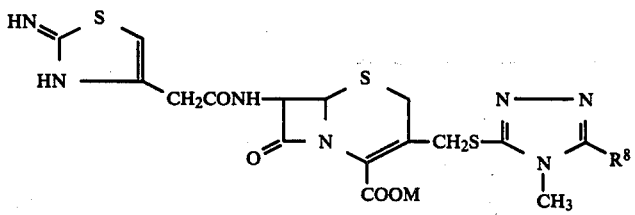

| Compound No. | R[8] | M | UVλ$_{max}$ (ε in water) | IR (KBr) cm$^{-1}$ | NMR δ ppm | Method No. |
|---|---|---|---|---|---|---|
| 31 | —NH$_2$ | Na | 257nm (1.43 × 10$^4$) | 1758 | (100MHz, in D$_2$O): 3.45 & 3.95(ABq, J18Hz,2-CH$_2$), 3.57 (s,N—CH$_3$), 3.68 & 4.36(ABq,J13Hz, 3-CH$_2$), 3.70(s, CH$_2$CO), 5.17(d, J5Hz,6-H), 5.72(d, J5Hz,7-H), 6.60(s, thiazole 5-H). | 4 |

TABLE 5

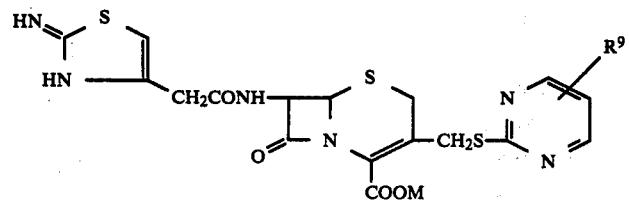

| Compound No. | R[9] | M | IR (KBr) cm$^{-1}$ | NMR δ ppm | Method No. |
|---|---|---|---|---|---|
| 32 | 4-NH$_2$,5-CH$_3$ | Na | 1758 | (100Mz, in D$_2$O): 2.04(s,CH$_3$), 3.43 & 3.74(ABq,J18Hz,2-CH$_2$), 3.66(s,CH$_2$CO), 3.91 & 4.57 (ABq,J14Hz,3-CH$_2$), 5.12(d,J5Hz, 6-H), 5.73(d,J5Hz,7-H), 6.52(s, thiazole 5-H), 7.79(s, pyrimidine-H). | 4 |
| 33 | 4-NH$_2$,6-OH | Na | 1758 | (100MHz, in D$_2$O): 3.52 & 3.80 (Abq,J18Hz,2-CH$_2$), 3.69(s, CH$_2$CO), 4.10 & 4.59(ABq,3-CH$_2$), 5.17(d,J5Hz,6-H), 5.75(d,J5Hz, 7-H), 6.55(s,thiazole-H). | 4 |
| 34 | 4-OH,6-CH$_3$ | Na | 1760 | (100MHz, in D$_2$O): 2.31(s,CH$_3$), 3.58 & 3.82(ABq,J18Hz,2-CH$_2$), 3.67(s,CH$_2$CO), 4.13 & 4.56(ABq, J14Hz,3-CH$_2$), 5.22(d,J5Hz,6-H), 5.75(d,J5Hz,7-H), 6.08(s, pyri- | 4 |

TABLE 5-continued

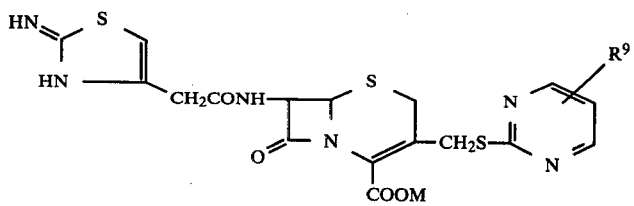

| Compound No. | $R^9$ | M | IR (KBr) cm$^{-1}$ | NMR δ ppm | Method No. |
|---|---|---|---|---|---|
| | | | | midine-H), 6.52(s,thiazole-H). | |

TABLE 6

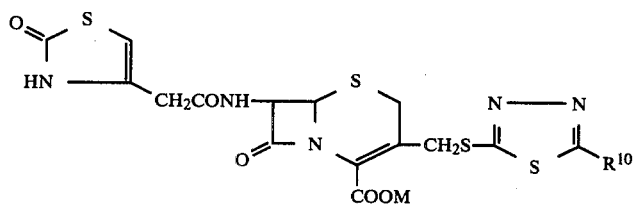

| Compound No. | $R^{10}$ | M | UVλ$_{max}$ (ε in water) | IR (KBr) cm$^{-1}$ | NMR δ ppm | Method No. |
|---|---|---|---|---|---|---|
| 35 | —NHCH$_3$ | H | in 5% NaHCO$_3$ 253nm (1.28 × 10$^4$) | 1780 | (100MHz, in d$_6$-DMSO): 2.85(s,NCH$_3$), 3.32(s, CH$_2$CO), 3.52 & 3.75 (ABq,J18Hz,2-CH$_2$), 4.04 & 4.24(ABq,J13Hz, 3-CH$_2$), 5.04 & 5.65 (each d,J4.5Hz,6- & 7-H), 6.00(s,thiazoline H), 8.89(d,J8Hz,NHCO). | 6 7 8 |
| 36 | —SCH$_2$CONH$_2$ | H | — | 1785 | (100MHz, in d$_6$-DMSO): 3.32(s,CH$_2$CO), 3.4–3.7 (m,2-CH$_2$), 3.96(s,SCH$_2$), 4.20 & 4.48(ABq,J13Hz, 3-CH$_2$), 5.07(d,J4.5Hz, 6-H), 5.67(dd,J4.5 & 8.0Hz, 7-H), 6.00(s, thiazoline H), 7.22 & 7.62(CONH$_2$). | 6 7 8 |
| 37 | —CH$_2$CON⟨morpholino⟩ | H | — | 1786 | (100MHz, in d$_6$-DMSO): 3.31(s,CH$_2$CO), 3.4–3.8 (m,5 × CH$_2$), 4.23 & 4.52 (ABq,J13Hz,3-CH$_2$), 4.29 (s,CH$_2$CO), 5.06(d,J4.5Hz, 6-H), 5.66(dd,J4.5 & 8.0 Hz,7-H), 6.0(s,thiazoline H), 8.96(d,J8.0Hz,NH). | 6 7 8 |

TABLE 7

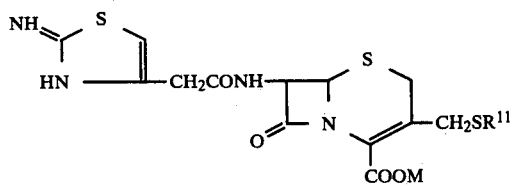

| Compound No. | R[11] | M | UVλ$_{max}$ (ε in water) | IR (KBr) cm$^{-1}$ | NMR δ ppm | Method No. |
|---|---|---|---|---|---|---|
| 38 | ![N—N oxadiazole with CH3] | Na | 258nm (1.56 × 10⁴) | 1763 | (100MHz, in D$_2$O): 2.57(s,oxadiazole CH$_3$), 3.42 & 3.82 (ABq,J18Hz,2-CH$_2$), 3.62(s,CH$_2$CO), 3.97 & 4.51(ABq,J13Hz,3-CH$_2$), 5.10(d,J5Hz,6-H), 5.67 (d,J5Hz,7-H), 6.51(s, thiazole 5-H). | 4 9 |
| 39 | ![N-methyl triazole] | Na | 261nm (1.49 × 10⁴) | 1765 | (100MHz, in D$_2$O): 3.47 & 3.90(ABq,17Hz,2-CH$_2$), 3.67(s,CH$_2$CO), 3.80(s, triazole CH$_3$), 3.83 & 4.37(ABq,J14Hz,3-CH$_2$), 5.15(d,J5Hz,6-H), 5.70(d,J5Hz,7-H), 6.56 (s,thiazole 5-H), 8.58 (s,triazole 5-H). | 4 |
| 40 | ![pyridazine N-oxide CH3] | Na | — | 1750 | (100MHz, in D$_2$O): 2.47 (s,pyridazine CH$_3$), 3.58(ABq,2-CH$_2$), 3.59 (s,CH$_2$CO), 4.20(ABq, 3-CH$_2$), 5.10(d,6-H), 5.65(d,7-H), 6.46(s, thiazole 5-H), 7.35 & 7.74(each d, pyridazine 4 & 5-H). | 3 9 |
| 41 | ![NH triazole] | Na | 259nm (1.46 × 10⁴) | 1768 | (100MHz, in D$_2$O): 3.45 & 3.77(ABq,J18Hz,2-CH$_2$), 3.62(s,CH$_2$CO), 4.03 & 4.27(ABq,J14Hz,3-CH$_2$), 5.12(d,5Hz,6-H), 5.67 (d,5Hz,7-H),6.50(s, triazole 4-H), 8.36 (s,triazole 5-H). | 4 |
| 42 | ![dimethyl triazole] | Na | 250nm (1.60 × 10⁴) | 1760 | (100MHz, in D$_2$O): 2.52 (s,triazole 5-CH$_3$), 3.43 & 3.95(ABq,J18Hz, 2-CH$_2$), 3.68(s,CH$_2$CO & triazole 4-CH$_3$), 3.74 & 4.41(ABq,J14Hz,3-CH$_2$), 5.14(d.J4Hz,6-H), 5.70 (d,J4Hz,7-H), 6.57(s, triazole 5-H). | 3 4 |
| 43 | ![N-methyl tetrazole] | H | — | 1762, 1662 | (100MHz, in d$_6$-DMSO): 3.39(s,CH$_2$CO), 3.55 & 3.77(ABq,J18Hz,2-CH$_2$), 3.90(s,tetrazole 1-CH$_3$), 4.21 & 4.36(ABq,J14Hz, 3-CH$_2$), 5.03(d,J5Hz, 6-H), 5.66(dd,J9 & 5Hz, 7-H), 6.23(s,thiazole 5-H), 6.2–7.1(m,NH$_2$), 8.85(d,J9Hz,CONH). | 1 2 |
| 44 | ![N-methyl 1,3-diazole] | Na | 250nm (1.57 × 10⁴) | 1758 | (100MHz, in D$_2$O): 3.32 & 3.85(ABq,J18Hz,2-CH$_2$), 3.68(s,CH$_2$CO), 3.65 & 4.35(ABq,J13Hz,3-CH$_2$), 3.79(s,1,3-diazole 1-CH$_3$), 5.13(d,J5Hz,6-H), 5.69(d,J5Hz,7-H), 6.57 (s,thiazole 5-H), 7.14 & 7.30(each d,J1Hz,1,3-diazole 4- & 5-H). | 4 |

TABLE 7-continued

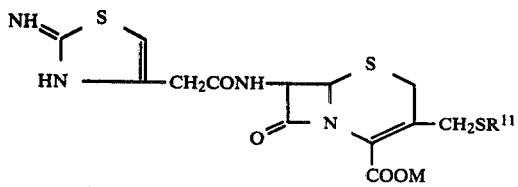

| Compound No. | $R^{11}$ | M | UV$\lambda_{max}$ ($\epsilon$ in water) | IR (KBr) cm$^{-1}$ | NMR $\delta$ ppm | Method No. |
|---|---|---|---|---|---|---|
| 45 | 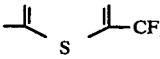 | Na | 261nm (1.59 × 10$^4$) | 1763 | (100MHz, in D$_2$O): 3.56 & 3.89(ABq, J18Hz,2-CH$_2$), 3.71 (s,CH$_2$CO), 4.32 & 4.70(ABq,J13Hz,3-CH$_2$), 5.21(d,J5Hz, 6-H), 5.78(d,J5Hz, 7-H), 6.58(s, thiazole 5-H). | 4 9 |
| 46 | 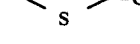 | Na | 258nm (1.61 × 10$^4$) | 1757 | (100MHz, in D$_2$O): 2.35 & 2.77(each s,thiazole 4- & 5-CH$_3$), 3.40 & 3.82(ABq,J18Hz, 2-CH$_2$), 3.69(s, CH$_2$CO), 3.89 & 4.51(ABq,J13Hz, 3-CH$_2$), 5.15(d, J5Hz,6-H), 5.75 (d,J5Hz,7-H), 6.56(s,thiazole 5-H). | 4 9 |
| 47 |  | H | (in 2% NaHCO$_3$) 259nm (1.61 × 10$^4$) | 1759 | (100MHz, in d$_6$-DMSO): 2.32(s, thiazole 4-CH$_3$), 3.99(s,CH$_2$CO), 3.50 & 3.77(ABq, J18Hz,2-CH$_2$), 4.10 & 4.48(ABq,J13Hz, 3-CH$_2$), 5.05(d, J5Hz,6-H), 5.67 (q,J5 & 8Hz,7-H), 6.23(s,thiazole 5-H), 6.85(broad s,NH$_2$), 7.15(s, thiazole 5-H), 8.82(d,J8Hz,CONH). | 4 9 |
| 48 |  | Na | 258nm (1.73 × 10$^4$) | 1758 | (100MHz, in D$_2$O): 2.55(s,thiazole 5-CH$_3$), 3.42 & 3.85(ABq,J18Hz, 2-CH$_2$), 3.70(s, CH$_2$CO), 3.90 & 4.56(ABq,J14Hz, 3-CH$_2$),5.15(d, J4.5Hz, 6-H),5.73 (d,J4.5Hz,7-H), 6.58(s,thiazole 5-H), 7.51(s, thiazole 4-H). | 4 9 |
| 49 |  | Na | — | 1765 | (60MHz, in D$_2$O): 3.28 & 3.64(ABq, J18Hz,2-CH$_2$), 3.50 (s, CH$_2$CO), 3.80 & 3.64(ABq,J14Hz, 3-CH$_2$), 4.95(d, J4.5Hz,6-H), 5.54 (d,J4.5Hz,7-H), 6.41(s,thiazole 5-H), 7.0–7.9(m, pyridine 3,4,5-H), 8.28(m,pyridine 6-H). | 4 |

TABLE 7-continued

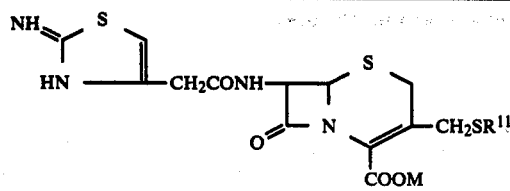

| Compound No. | $R^{11}$ | M | UV$\lambda_{max}$ ($\epsilon$ in water) | IR (KBr) cm$^{-1}$ | NMR $\delta$ ppm | Method No. |
|---|---|---|---|---|---|---|
| 50 | ![pyrimidine] | Na | — | 1763 | (60MHz, in D$_2$O): 3.63(s,CH$_2$CO), 3.42 & 3.95(ABq,J18Hz, 2-CH$_2$), 3.85 & 4.35 (ABq,J14Hz,3-CH$_2$) 5.01(d,J5Hz,6-H), 5.60(d,J5Hz,7-H), 6.40(s,thiazole 5-H), 7.15(t,J5.5Hz, pyrimidine 5-H), 8.47(d,J5.5Hz,pyrimidine 4- & 6-H). | 4 |

TABLE 8

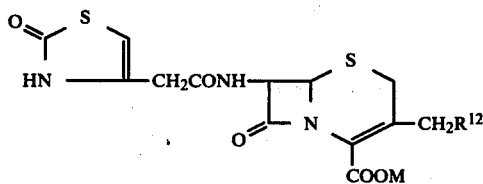

| Compound No. | $R^{12}$ | M | UV$\lambda_{max}$ ($\epsilon$ in water) | IR (KBr) cm$^{-1}$ | NMR $\delta$ ppm | Method No. |
|---|---|---|---|---|---|---|
| 51 | -S-(pyridazine-CH$_3$, N-N→O) | Na | — | 1760 | (100MHz, in D$_2$O): 2.48(s,pyridazine-CH$_3$), 3.61(s,CH$_2$CO), 3.64(ABq,2-CH$_2$), 4.20(ABq,3-CH$_2$), 5.10(d,6-H), 5.64 (d,7-H), 6.25(s, thiazoline 5-H), 7.37 & 7.71(each d, pyridazine 4 & 5-H) | 4 |
| 52 | -S-(thiazole-CH$_3$) | Na | — | 1760 | (100MHz, in D$_2$O): 2.48(s,thiazole 4-CH$_3$), 3.43 & 3.86(ABq, J18Hz, 2-CH$_2$), 3.70(s, CH$_2$CO), 3.95 & 4.59(ABq,J13Hz, 3-CH$_2$),5.15(d, J4.5Hz, 6-H), 5.72(d,J4.5Hz, 7-H), 6.34(s, thiazoline 5-H), 7.21(s,thiazole 5-H). | 4 |
| 53 | —O—COCH$_3$ | H | | | identical with those of Example 1 | 8 |
| 54 | -S-(N-N, O, CH$_3$) | H | | | identical with those of Example 6 | 8 |
| 55 | -S-(N-N, S, CH$_3$) | H | | | identical with those of Example 9 | 8 |

TABLE 8-continued

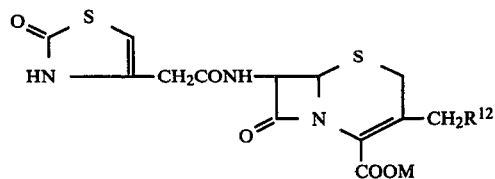

| Compound No. | R$^{12}$ | M | UVλ$_{max}$ (ε in water) | IR (KBr) cm$^{-1}$ | NMR δ ppm | Method No. |
|---|---|---|---|---|---|---|
| 56 | -S-(thiadiazole) | H | | | identical with those of Example 4 | 8 |
| 57 | -S-(N-methyl tetrazole) | H | | | identical with those of Example 2 | 8 |

TABLE 9

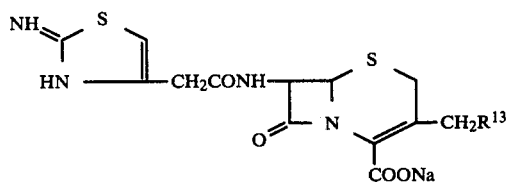

| Compound No. | R$^{13}$ | UVλ$_{max}$ (ε in water) | IR (KBr) cm$^{-1}$ | NMR δ ppm | Method No. |
|---|---|---|---|---|---|
| 58 | -S-(4,5-dimethyloxazole) | 255nm (1.87 × 10$^4$) | 1757 | (100MHz, in D$_2$O): 2.14 & 2.34(each s, oxazole 4- & 5-CH$_3$), 3.42 & 3.87(ABq, J18Hz, 2-CH$_2$), 3.70(s, CH$_2$CO), 3.91 & 4.57(ABq, J14Hz, 3-CH$_2$), 5.16(d, J5Hz, 6-H), 5.75(d, J5Hz, 7-H), 6.58(s, thiazole 5-H). | 9 |
| 59 | —OCOCH$_3$ | | | identical with those of Example 11 | 9 |
| 60 | -S-(N-methyl tetrazole) | | | identical with those of Example 16 | 9 |
| 61 | -S-(methylthiadiazole) | | | identical with those of Example 18 | 9 |
| 62 | -S-(thiadiazole) | | | identical with those of Example 14 | 9 |

TABLE 10

[Structure: thiazoline-CH=C(NH-)-CH₂CONH-cephem core with CH₂R¹⁴ at 3-position and COONa]

| Compound No. | R¹⁴ | UV λ$_{max}$ (ε in water) | NMR δ ppm | Method No. |
|---|---|---|---|---|
| 63 | —OCOCH₃ | 250nm (8.39 × 10³) 310nm (1.16 × 10⁴) | (100MHz, in D₂O): 2.18 (s,CH₃CO), 3.44 & 3.76 (ABq,J18Hz,2-CH₂), 3.76 (s,CH₂CO), 4.78 & 4.98 (ABq,J13Hz,3-CH₂), 5.10 (d,J5Hz,6-H), 5.75(d,J5Hz, 7-H), 6.87(s,thiazoline 5-H). | 10 |
| 64 | —S—C(=N-N(CH₃)-N=N) (1-methyltetrazol-5-ylthio) | 270nm (1.03 × 10⁴) 310nm (8.80 × 10³) | (100MHz, in D₂O): 3.48 & 3.81(ABq,J18Hz,2-CH₂), 3.75(s,CH₂CO), 4.09(s, tetrazole CH₃), 4.39(ABq, J13Hz,3-CH₂), 5.13(d,J5Hz, 6-H), 5.67(d,J5Hz,7-H), 6.84(s,thiazoline 5-H). | 10 |

TABLE 11

Antibacterial spectra (mcg./ml., agar dilution method)

| Compound No. | Gram-positive bacteria | | Gram-negative bacteria | | | | | |
|---|---|---|---|---|---|---|---|---|
| | S. aureus 209P | S. aureus 1840 | E. coli NIHJ JC-2 | E. coli 0-111 | K. pneumoniae T-7 | E. coli mo-niae DT | P. vulgaris IFO 3988 | P. morganii Eb53 |
| Cephaloridine | ≦0.2 | 0.39 | 3.13 | 1.56 | >100 | 1.56 | 6.25 | >100 |
| Cephazolin | ≦0.2 | 0.78 | 1.56 | 0.78 | 50 | 1.56 | 6.25 | 100 |
| 4 | 0.2 | 0.78 | 0.78 | 0.1 | 100 | 0.2 | 0.2 | 50 |
| 6 | ≦0.2 | 0.78 | 0.78 | ≦0.2 | 12.5 | ≦0.2 | 0.39 | 6.25 |
| 7 | 0.78 | 3.13 | 0.78 | ≦0.2 | 25 | ≦0.2 | 0.39 | 12.5 |
| 8 | 0.39 | 0.78 | 0.78 | ≦0.2 | 12.5 | ≦0.2 | 0.39 | <0.2 |
| 9 | ≦0.2 | 0.78 | 1.56 | 0.39 | 50 | ≦0.2 | 6.25 | <0.2 |
| 12 | 0.39 | 1.56 | 0.78 | ≦0.2 | 50 | ≦0.2 | ≦0.2 | 25 |
| 15 | 0.78 | 1.56 | 0.78 | ≦0.2 | 25 | ≦0.2 | ≦0.2 | 3.13 |
| 16 | ≦0.2 | 0.78 | 0.39 | ≦0.2 | 12.5 | ≦0.2 | ≦0.2 | 1.56 |
| 17 | 0.39 | 3.13 | 0.39 | ≦0.2 | 12.5 | ≦0.2 | 0.39 | 0.78 |
| 18 | 1.56 | 3.13 | 0.78 | ≦0.2 | 6.25 | ≦0.2 | 1.56 | 1.56 |
| 19 | 0.78 | 3.13 | 0.78 | ≦0.2 | 25 | ≦0.2 | ≦0.2 | 0.78 |
| 21 | ≦0.2 | 1.56 | 0.39 | ≦0.2 | 25 | ≦0.2 | ≦0.2 | 0.78 |
| 22 | 0.78 | 3.13 | 0.78 | ≦0.2 | 25 | ≦0.2 | ≦0.2 | 0.78 |
| 23 | ≦0.2 | 0.78 | 1.56 | 0.39 | 25 | ≦0.2 | 0.39 | 3.13 |
| 24 | ≦0.2 | 0.78 | 1.56 | 0.39 | 25 | ≦0.2 | 0.39 | 25 |
| 25 | 0.39 | 0.78 | 0.39 | ≦0.2 | 100 | ≦0.2 | 0.39 | 25 |
| 28 | 0.39 | 1.56 | 0.39 | ≦0.2 | 3.13 | ≦0.2 | 0.78 | ≦0.2 |
| 29 | 0.78 | 1.56 | 0.39 | ≦0.2 | 3.13 | ≦0.2 | ≦0.2 | ≦0.2 |
| 30 | 0.39 | 1.56 | 1.56 | 0.39 | 100 | <0.05 | 0.2 | 50 |
| 31 | 0.78 | 1.56 | 0.2 | ≦0.1 | 3.13 | ≦0.1 | 0.2 | 1.56 |
| 32 | 0.2 | 1.56 | 1.56 | 0.78 | 50 | 0.39 | 0.78 | 100 |
| 38 | 0.39 | 0.78 | 1.56 | 0.39 | — | 0.39 | — | 25 |
| 39 | 0.78 | 1.56 | 0.2 | <0.05 | 25 | 0.1 | — | 25 |
| 40 | 0.2 | 0.78 | 0.39 | 0.2 | — | 0.1 | — | 3.125 |
| 51 | 0.2 | 0.78 | 1.56 | 0.78 | — | 1.56 | — | 12.5 |
| 41 | 0.39 | 0.78 | 0.78 | 0.78 | — | 0.2 | — | 25 |
| 42 | 0.39 | 1.56 | 0.2 | 0.1 | — | 0.1 | — | 1.56 |
| 44 | 0.39 | 1.56 | 0.78 | 0.39 | 6.25 | 0.39 | 0.39 | — |
| 45 | ≦0.2 | 0.78 | 3.13 | 0.78 | 25 | 0.78 | 0.78 | — |
| 47 | ≦0.2 | 0.78 | 1.56 | 0.78 | 12.5 | 0.39 | 0.39 | — |
| 55 | 0.2 | 0.78 | 1.56 | 0.78 | — | 1.56 | — | — |
| 64 | <0.78 | 1.56 | — | 1.56 | — | <0.78 | — | — |

TABLE 12

Protective Effect (ED₅₀*, mg/kg) on Infected Mice

| Compound No. | ED₅₀* mg/kg |
|---|---|
| 9 | 0.812 |
| 11 | <0.625 |
| 19 | <0.625 |
| 21 | <0.625 |
| Cephaloridine | 2.81 |

TABLE 13

| Compound No. | ED₅₀* mg/kg |
|---|---|
| 12 | <0.625 |
| 15 | <0.625 |
| 16 | <0.625 |
| 17 | <0.625 |
| 18 | <0.625 |
| Cephaloridine | 1.94 |

TABLE 14

| Compound No. | ED₅₀* mg/kg |
|---|---|
| 40 | 0.28 |
| 42 | 0.38 |
| 39 | 0.73 |
| 60 | 0.89 |
| 62 | 2.38 |
| Cephaloridine | 3.57 |
| Cephazolin | 3.1 |

*Test animals: male mice (ICR/SLC) 5 mice per group per single dose
Infection: intraperitoneally with *Escherichia coli* 0-111
Administration: a single subcutaneous dose immediately after challenge
Observation period: 7 days

EXAMPLE 24

(1) A solution of 0.263 g. of (2-thioxo-4-thiazolin-4-yl) acetic acid dissolved in 3 ml. of dimethylformamide is cooled with ice and to the solution are added 0.173 g. of N-hydroxysuccinimide and 0.309 g. of dicyclohexylcarbodiimide, followed by stirring for 25 minutes. The reaction mixture is subjected to filtration under suction to remove the precipitate of N,N'-dicyclohexylurea and 1 ml. each of dimethylformamide and dichloromethane are added to the filtrate.

(2) The mixed solution is added at a stroke to a solution of 0.49 g. of 7-aminocephalosporanic acid and 0.252 ml. of triethylamine dissolved in 5 ml. of dichloromethane and the mixture is stirred for 3 hours at room temperature. The solvent is distilled off under reduced pressure and water is added to the residue. The pH of the resultant mixture is adjusted to 2.5 by adding concentrated phosphoric acid under ice-cooling, followed by extracting with ethyl acetate (60 ml. ×3). The combined ethyl acetate layer is dried and concentrated to dryness under reduced pressure. The residue is dissolved in a solution of 0.168 g. of sodium hydrogen carbonate dissolved in 5 ml. of water and the solution is chromatographed on a column of polystyrene resin (Amberlite XAD-2), followed by development with water. The fractions containing the desired product are pooled and freeze-dried to obtain sodium 7-[2-(2-thioxo-4-thiazolin-4-yl)acetamido]-3-acetoxymethyl-3-cephem-4-carboxylate, which is in good agreement with the Compound No. 64 of Example 21 in IR, UV and NMR spectra. Yield 0.302 g. (45%).

EXAMPLE 25

Preparation of 7-(4-chloro-3-oxobutyrylamido)3-acetoxymethyl-3-cephem-4-carboxylic acid A solution of 4.4 g. of diketene in 10 ml. of methylene chloride is previously chilled to −35° C. and 3.92 g. of chlorine is passed into the solution. The reaction mixture is stirred for 15 minutes. Meanwhile, 10.9 g. of 7-aminocephalosporanic acid and 8.1 g. of triethylamine are dissolved in 100 ml. of methylene chloride and the solution is chilled to −30° C. To this solution is added the above-prepared reaction mixture under stirring and cooling so that the temperature will not rise beyond −30° C. Then, the temperature of the mixture is gradually increased to room temperature over a period of one hour, after which the solvent is distilled off under reduced pressure. To the residue is added 100 ml. of ethyl acetate and the mixture is shaken vigorously with 100 ml. of a 10% aqueous solution of phosphoric acid. The water layer is taken, saturated with sodium chloride and extracted three times with ethyl acetate. The ethyl acetate layers are pooled, washed with a saturated aqueous solution of sodium chloride, dehydrated and concentrated under reduced pressure to a final volume of 20 ml. The concentrate is allowed to stand in the cold and the resultant crystals are recovered by filtration. The described procedure gives the above-indicated compound.

Yield 6.3 g. Melting point: 135°–140° C. (decomp.).
IR(cm$^{-1}$, KBr): 1790, 1750, 1655.
NMR($\delta$ in d$_6$-DMSO): 2.00(s,COCH$_3$), 3.41 & 3.64(ABq, J18 Hz, 2-CH$_2$), 3.56(s,COCH$_2$CO), 4.50(s,ClCH$_2$-), 4.67 & 5.00 (ABq, J13 Hz, 3-CH$_2$), 5.07(d, J4.5 Hz, 6-H), 5.66(dd, J4.5 & 8 Hz, 7-H), 9.04(d, J8 Hz, CONH).
Elemental analysis: Calcd. for C$_{14}$H$_{15}$ClN$_2$O$_7$S: C, 43.03; H, 3.87; N, 7.17. Found: C, 43.01; H, 3.89; N, 7.18.

EXAMPLE 26

Preparation of 7-(4-bromo-3-oxobutyrylamido)-3-acetoxymethyl-3-cephem-4-carboxylic acid A solution of 3.4 g. of diketene in 10 ml. of methylene chloride is previously chilled to −30° C. and a solution of 6.4 g. of bromine in 10 ml. of methylene chloride is added dropwise. Meanwhile, 10.9 g. of 7-aminocephalosporanic acid and 8.1 g. of triethylamine are dissolved in 100 ml. of methylene chloride and the solution is chilled to −30° C. To this solution is added the above-prepared reaction mixture under stirring and cooling so that the temperature of the mixture will not exceed −30° C.

The temperature is gradually increased to room temperature over a period of one hour, after which the solvent is distilled off under reduced pressure. To the residue is added 100 ml. of ethyl acetate and the mixture is shaken vigorously with 100 ml. of a 10% aqueous solution of phosphoric acid. The water layer is taken, saturated with sodium chloride and extracted twice with ethyl acetate. The ethyl acetate layers are pooled, washed with a saturated aqueous solution of sodium chloride, dehydrated, treated with activated carbon and concentrated to dryness under reduced pressure. To the residue is added ether and the mixture is allowed to stand.

The resultant crystals are recovered by filtration under suction. The procedure gives the above-indicated compound. This product includes a quarter of a mole of ethyl acetate as the solvent of crystallization. Yield 8 grams.

IR(cm$^{-1}$, KBr): 1780, 1735, 1650.
NMR($\delta$ in d$_6$-DMSO): 2.01(s,CH$_3$CO), 3.54(m,2-CH$_2$), 3.62(s,COCH$_2$CO), 4.37(s,BrCH$_2$CO), 4.67 & 5.01 (ABq, J14 Hz, 3-CH$_2$), 5.08(d, J4 Hz, 6-H), 5.66(dd, J4 & 8 Hz, 7-H), 9.04(d, J8 Hz, CONH).
Elemental analysis: Calc. for C$_{14}$H$_{15}$BrN$_2$O$_7$S.¼ C$_4$H$_8$O$_2$: C, 39.40; H, 3.75; N, 6.13. Found: C, 39.20; H, 3.63; N, 6.03.

EXAMPLE 27

Production of 7-amino-3-(2-methylsulfonylmethyl-1,3,4-thiadiazol-5-yl)thiomethyl-3-cephem-4-carboxylic acid (1) A solution of 4.9 g. of potassium hydroxide in 30 ml. of methanol is stirred under ice-cooling and to the solution are added 12.5 g. of methylsulfonyl-acetylhydrazide and 5.3 ml. of carbondisulfide, followed by stirring for 30 minutes under ice-cooling and then for 30 minutes at the room temperature. Methanol is distilled off from the reaction mixture and to the residue is triturated with the addition of ethanol to give precipitate. The precipitate is collected by filtration and dried to obtain 20.39 g. of potassium 3-(methylsulfonylacetyl) dithiocarbazinate as crystalline powder.

(2) In 40 ml. of concentrated sulfuric acid cooled with ice is dissolved 8.0 g. of potassium 3-(methylsulfonylacetyl)dithiocarbazinate, and the mixture is stirred for 10 minutes under ice-cooling. The reaction mixture is poured onto 150 g. of ice and the mixture is stirred to give precipitate, which is collected by filtration and washed with cold water, followed by drying. The procedure yields 2.29 g. of 2-methylsulfonylmethyl-1,3,4-thiadiazole-5-thiol. Melting point; 204°–206° C. (decomp.)

IR(cm$^{-1}$, nujol): 1315, 1139.
NMR(100 MHz, in d$_6$-DMSO): $\delta$ 3.08(s, CH$_3$), 4.56(broad s, SH), 4.89(s, CH$_2$).
Elemental analysis: Calculated for C$_4$H$_6$N$_2$O$_2$S$_3$: C, 22.84; H, 2.288; N, 13.32. Found: C, 22.97; H, 2.85; N, 13.18.

(3) 2-methylsulfonylmethyl-1,3,4-thiadiazole-5-thiol is treated in a similar manner to Method 1 of Example 23 to obtain 7-amino-3-(2-methylsulfonylmethyl-1,3,4-thiadiazol-5-yl)thiomethyl-3-cephem-4-carboxylic acid.

IR(cm$^{-1}$, KBr): 1800.

EXAMPLE 28

In a similar manner to Example 27, the following compounds are prepared;

TABLE 15

N———N
$R^{16}$—S—⟨ ⟩—$R^{15}$
         S

| $R^{15}$ | $R^{16}$ | Melting point (°C.) | $R^{16}$ | IR (cm$^{-1}$, KBr) |
|---|---|---|---|---|
| CH$_3$SCH$_2$— | H | 105–107 (recrystallized from ethyl acetate) | * | 1800 |
| NH$_2$COCH$_2$— | H | 179–182 (decomp.) | * | 1800 |
| CH$_3$OCOCH$_2$— | H | 79–80 (recrystallized from benzene) | * | 1800 |
| HOOCCH$_2$— | H | 166–168 (decomp., recrystallized from ethyl acetate-benzene) | * | 1800 |
| O⟨ ⟩N—CH$_2$— | H | — | * | 1800 |
| (CH$_3$)$_2$NCOCH$_2$— | H | — | * | 1800 |

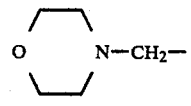

EXAMPLE 29

Production of 7-amino-3-[2-(2-hydroxyethylamino)-1,3,4-thiadiazol-5-yl]thiomethyl-3-cephem-4-carboxylic acid (1) A solution of 12.2 g. of methyl dithiocarbazinate and 18.3 g. of 2-aminoethanol in 25 ml. of water is heated at 95° C. for 5 hours. After cooling, 10 ml. of acetic acid is added to the reaction mixture and the mixture is allowed to stand in a refrigerator overnight to precipitate crystalline, which is collected by filtration and dried to obtain 2.85 g. of 4-(2-hydroxyethyl)thiosemicarbazide.

(2) A mixed solution of 1.35 g. of 4-(2-hydroxyethyl)-thiosemicarbazide, 1.14 g. of carbon disulfide and 20 ml. of pyridine is heated to reflux for 5 hours under stirring and the reaction mixture is concentrated to dryness under reduced pressure. To the residue is added water to precipitate crystals which are collected by filtration to obtain 1.35 g. of 2-(2-hydroxyethylamino)-1,3,4-thiadiazole-5-thiol.

NMR(60 MHz, in DMSO): δ 3.19 (t, CH$_2$), 3.46(t, CH$_2$), 7.33(broad s, OH).

(3) 2-(2-hydroxyethylamino)-1,3,4-thiadiazole-5-thiol is treated in a similar manner to Method 2 of Example 23 to obtain the above-indicated compound.

IR(cm$^{-1}$, KBr): 1800.

EXAMPLE 30

In a similar manner to Example 29, the following compounds are prepared;

TABLE 16

N———N
$R^{16}$—S—⟨ ⟩—$R^{15}$
         S

| $R^{15}$ | $R^{16}$ | NMR δ (60 MHz) | $R^{16}$ | IR (cm$^{-1}$, KBr) |
|---|---|---|---|---|
| (CH$_3$)$_2$NC$_2$H$_4$NH— | H | (in DMSO) 2.90(s, 2 × CH$_3$), 3.40(t, CH$_2$), 4.28(t, CH$_2$) | * | 1800 |
| HSO$_3$C$_2$H$_4$NH— | H | (in D$_2$O) 3.17(t, CH$_2$), 3.78(t, CH$_2$) | * | 1795 |

*The same as in Table 15

EXAMPLE 31

Production of 7-amino-3-[2-(2-hydroxyethylthio)-1,3,4-thiadiazol-5-yl]thiomethyl-3-cephem-4-carboxylic acid (1) Into a solution of 3.0 g. of 1,3,4-thiadiazole-2,5-dithiol dissolved in 22 ml. of 0.1 N aqueous solution of sodium hydroxide is dropped 2.5 g. of ethylenebromhydrine under ice-cooling and stirring. The mixture is allowed to stand overnight at a room temperature to precipitate pale-yellowish needles, which are collected by filtration under suction and dried to obtain 3.0 g. of 2-(2-hydroxyethylthio)-1,3,4-thiadiazol-5-thiol melting at 112°–113° C.

IR (cm$^{-1}$, KBr): 1500, 1280, 1055.

NMR(60 MHz, in NaHCO$_3$-D$_2$O): δ 3.50(t, CH$_2$), 4.60(t, CH$_2$).

(2) The product above (1) is treated in a similar manner to Method 2 of Example 23 to obtain the above indicated compound.

IR (cm$^{-1}$, KBr): 1800.

NMR(60 MHz, in NaHCO$_3$ -D$_2$O): 3.54(t, J6 Hz, CH$_2$), 3.54 & 3.73(ABq, J16 Hz, 2-CH$_2$), 3.91(t, J6 Hz, CH$_2$), 4.07 & 4.38 (ABq, J13 Hz, 3-CH$_2$), 5.05 (d, J5 Hz, 6-H), 5.45(d, J5 Hz, 7-H).

EXAMPLE 32

In a similar manner to Example 31, the following compounds are prepared;

TABLE 17

N———N
$R^{16}$—S—⟨ ⟩—$R^{15}$
         S

| $R^{15}$ | $R^{16}$ | IR (cm$^{-1}$, KBr) | $R^{16}$ | IR (cm$^{-1}$, KBr) |
|---|---|---|---|---|
| HSO$_3$C$_2$H$_4$S— | H | 1190, 1040 | * | 1800 |
| NH$_2$COCH$_2$S— | H | 1685 | * | 1800 |
| CH$_3$COCH$_2$S— | H | — | * | 1800 |
| CH$_3$OC$_2$H$_4$S— | H | 1720 | * | 1800 |
| C$_2$H$_5$OCOCH$_2$S— | H | 1705 | * | 1800 |
| (CH$_3$)$_2$NC$_2$H$_4$S— | H | — | * | 1800 |
| ⟨phenyl⟩—COOC$_2$H$_4$S— | H | — | * | 1795 |

*The same as in Table 15.

What is claimed is:

1. A compound of the formula:

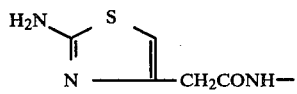
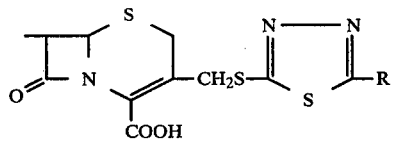

wherein R represents hydrogen, a $C_{1-12}$ alkyl, trifluoromethyl, amino, mercapto, carboxymethyl, carbamoylmethyl, N-$C_{1-12}$ alkylcarbamoylmethyl, $C_{1-12}$ alkoxycarbonylmethyl, methylthiomethyl, methylsulfonylmethyl, N-$C_{1-12}$ alkylamino-$C_{1-12}$ alkyl, morpholinomethyl, sulfo-$C_{1-12}$ alkylamine, hydroxy-$C_{1-12}$ alkylamino, $C_{1-12}$ alkylamino-$C_{1-12}$ alkylamino, $C_{1-12}$ alkoxycarbonylamino, 2-hydroxyethylthio, 2-$C_{1-12}$ acyloxy-ethylthio, carboxymethylthio, $C_{1-12}$ alkoxycarbonylmethylthio, carbamoylmethylthio, N-$C_{1-12}$ alkylcarbamoylmethylthio, acetylmethylthio, N-$C_{1-12}$ alkylamino-$C_{1-12}$-alkylthio, morpholinocarbonylmethylthio or 2-sulfoethylthio, or a pharmaceutically acceptable salt thereof.

2. A compound according to claim 1, namely, 7-[2-(2-aminothiazol-4-yl)acetamido]-3-(2-amino-1,3,4-thiadiazol-5-yl)thiomethyl-3-cephem-4-carboxylic acid.

3. A compound according to claim 1, namely, 7-[2-(2-aminothiazol-4-yl)acetamido]-3-[2-(2-hydroxylethylthio)-1,3,4-thiadiazol-5-yl]thiomethyl-3-cephem-4-carboxylic acid.

4. A compound according to claim 1, namely, 7-[2-(2-aminothiazol-4-yl)acetamido]-3-[2-(2-acetoxyethylthio)-1,3,4-thiadiazol-5-yl]thiomethyl-3-cephem-4-carboxylic acid.

5. A compound according to claim 1, namely, 7-[2-(2-aminothiazol-4-yl)acetamido]-3-[2-(2-caproyloxyethylthio)-1,3,4-thiadiazol-5-yl]thiomethyl-3-cephem-4-carboxylic acid.

6. A compound according to claim 1, namely, 7-[2-(2-aminothiazol-4-yl)acetamido]-3-[2-N,N-dimethylaminocarbonyl)methyl-1,3,4-thiadiazol-5-yl]thiomethyl-3-cephem-4-carboxylic acid.

7. A compound according to claim 1, namely, 7-[2-(2-aminothiazol-4-yl)acetamido]-3-[2-(2-N,N-dimethylaminoethyl)thio-1,3,4-thiadiazol-5-yl]thiomethyl-3-cephem-4-carboxylic acid.

8. A compound according to claim 1, namely, 7-[2-(2-aminothiazol-4-yl)acetamido]-3-[2-(2-sulfoethyl)thio-1,3,4-thiadiazol-5-yl]thiomethyl-3-cephem-4-carboxylic acid.

9. A compound according to claim 1, namely, 7-[2-(2-aminothiazol-4-yl)acetamido]-3-(2-carboxylmethylthio-1,3,4-thiadiazol-5-yl)thiomethyl-3-cephem-4-carboxylic acid.

10. A compound according to claim 1, namely, 7-[2-(2-aminothiazol-4-yl)acetamido]-3-(2-ethoxycarbonylmethylthio-1,3,4-thiadiazol-5-yl)thiomethyl-3-cephem-4-carboxylic acid.

11. A compound according to claim 1, namely, 7-[2-(2-aminothiazol-4-yl)acetamido]-3-(2-hexyloxycarbonylmethylthio-1,3,4-thiadiazol-5-yl)thiomethyl-3-cephem-4-carboxylic acid.

12. A compound according to claim 1, namely, 7-[2-(2-aminothiazol-4-yl)acetamido]-3-(2-carbamoylmethylthio-1,3,4-thiadiazol-5-yl)thiomethyl-3-cephem-4-carboxylic acid.

13. A compound according to claim 1, namely, 7-[2-(2-aminothiazol-4-yl)acetamido]-3-[2-(2-hydroxyethyl)amino-1,3,4-thiadiazol-5-yl]thiomethyl-3-cephem-4-carboxylic acid.

14. A compound according to claim 1, namely, 7-[2-(2-aminothiazol-4-yl)acetamido]-3-[2-(2-N,N-dimethylaminoethyl)amino-1,3,4-thiadiazol-5-yl]thiomethyl-3-cephem-4-carboxylic acid.

15. A compound according to claim 1, namely, 7-[2-(2-aminothiazol-4-yl)acetamido]-3-(2-carboxymethyl-1,3,4-thiadiazol-5-yl)thiomethyl-3-cephem-4-carboxylic acid.

16. A compound according to claim 1, namely, 7-[2-(2-aminothiazol-4-yl)acetamido]-3-(2-carbamoylmethyl-1,3,4-thiadiazol-5-yl)thiomethyl-3-cephem-4-carboxylic acid.

17. A compound according to claim 1, namely, 7-[2-(2-aminothiazol-4-yl)acetamido]-3-[2-(2-sulfoethyl)amino-1,3,4-thiadiazol-5-yl]thiomethyl-3-cephem-4-carboxylic acid.

18. A compound according to claim 1, namely, 7-[2-(2-aminothiazol-4-yl)acetamido]-3-(2-methyl-1,3,4-thiadiazol-5-yl)thiomethyl-3-cephem-4-carboxylic acid.

19. A compound according to claim 1, namely, 7-[2-(2-aminothiazol-4-yl)acetamido]-3-(1,3,4-thiadiazol-2-yl)thiomethyl-3-cephem-4-carboxylic acid.

20. A compound according to claim 1, namely, 7-[2-(2-aminothiazol-4-yl)acetamido]-3-(2-methylthiomethyl-1,3,4-thiadiazol-5-yl)thiomethyl-3-cephem-4-carboxylic acid.

* * * * *